(12) United States Patent
Telfort et al.

(10) Patent No.: US 10,463,340 B2
(45) Date of Patent: Nov. 5, 2019

(54) ACOUSTIC RESPIRATORY MONITORING SYSTEMS AND METHODS

(75) Inventors: Valery G. Telfort, Montreal (CA); Mark Wylie, Dorval (CA)

(73) Assignee: Masimo Corporation, Irvine, CA (US)

(*) Notice: Subject to any disclaimer, the term of this patent is extended or adjusted under 35 U.S.C. 154(b) by 227 days.

(21) Appl. No.: 12/904,789

(22) Filed: Oct. 14, 2010

(65) Prior Publication Data

US 2011/0125060 A1 May 26, 2011

Related U.S. Application Data

(60) Provisional application No. 61/252,099, filed on Oct. 15, 2009.

(51) Int. Cl.
*A61B 7/00* (2006.01)

(52) U.S. Cl.
CPC .................... *A61B 7/003* (2013.01)

(58) Field of Classification Search
USPC ............................. 600/586; 381/67; 704/500
See application file for complete search history.

(56) References Cited

U.S. PATENT DOCUMENTS

| | | | |
|---|---|---|---|
| 2,699,465 A | 1/1955 | Selden | |
| 3,399,467 A | 9/1968 | Ravin | |
| 3,682,161 A | 8/1972 | Alibert | |
| 3,867,925 A | 2/1975 | Ersek | |
| 3,951,230 A | 4/1976 | Littmann | |
| 3,991,304 A | 11/1976 | Hillsman | |
| 4,127,749 A | 11/1978 | Atoji et al. | |
| 4,254,302 A | 3/1981 | Walshe | |

(Continued)

FOREIGN PATENT DOCUMENTS

| | | |
|---|---|---|
| CA | 2490438 | 1/2004 |
| CA | 2262236 | 4/2008 |

(Continued)

OTHER PUBLICATIONS

US 8,740,816 B2, 06/2014, Telfort et al. (withdrawn)

(Continued)

*Primary Examiner* — Christian Jang
*Assistant Examiner* — Mitchell Alter
(74) *Attorney, Agent, or Firm* — Knobbe, Martens, Olson & Bear, LLP

(57) ABSTRACT

An acoustic sensor is provided according to certain aspects for non-invasively detecting physiological acoustic vibrations indicative of one or more physiological parameters of a medical patient. The sensor can include an acoustic sensing element configured to generate a first signal in response to acoustic vibrations from a medical patient. The sensor can also include front-end circuitry configured to receive an input signal that is based at least in part on the first signal and to produce an amplified signal in response to the input signal. In some embodiments, the sensor further includes a compression module in communication with the front-end circuitry and configured to compress portions of at least one of the input signal and the amplified signal according to a first compression scheme, the compressed portions corresponding to portions of the first signal having a magnitude greater than a predetermined threshold level.

24 Claims, 15 Drawing Sheets

(56) References Cited

U.S. PATENT DOCUMENTS

| | | | |
|---|---|---|---|
| 4,326,143 A | 4/1982 | Guth et al. | |
| 4,401,125 A | 8/1983 | Taylor et al. | |
| 4,413,202 A | 11/1983 | Krempl et al. | |
| 4,537,200 A | 8/1985 | Widrow | |
| 4,576,179 A | 3/1986 | Manus et al. | |
| 4,578,613 A | 3/1986 | Posthuma de Boer et al. | |
| 4,634,917 A | 1/1987 | Dvorksy et al. | |
| 4,653,498 A | 3/1987 | New, Jr. et al. | |
| 4,672,976 A | 6/1987 | Kroll | |
| 4,805,633 A | 2/1989 | Kotani et al. | |
| 4,827,943 A | 5/1989 | Bornn et al. | |
| 4,871,046 A | 10/1989 | Turner | |
| 4,884,809 A | 12/1989 | Rowan | |
| 4,924,876 A * | 5/1990 | Cameron | 600/538 |
| 4,947,853 A | 8/1990 | Hon | |
| 4,947,859 A | 8/1990 | Brewer et al. | |
| 4,960,118 A | 10/1990 | Pennock | |
| 4,960,128 A | 10/1990 | Gordon et al. | |
| 4,964,408 A | 10/1990 | Hink et al. | |
| 4,982,738 A | 1/1991 | Griebel | |
| 5,003,605 A | 3/1991 | Phillipps et al. | |
| 5,033,032 A | 7/1991 | Houghtaling | |
| 5,036,857 A | 8/1991 | Semmlow et al. | |
| 5,041,187 A | 8/1991 | Hink et al. | |
| 5,069,213 A | 12/1991 | Polczynski | |
| 5,078,151 A | 1/1992 | Laballery | |
| 5,140,992 A | 8/1992 | Zuckerwar et al. | |
| 5,143,078 A | 9/1992 | Mather et al. | |
| 5,163,438 A | 11/1992 | Gordon et al. | |
| 5,269,314 A | 12/1993 | Kendall et al. | |
| 5,278,627 A | 1/1994 | Aoyagi et al. | |
| 5,319,355 A | 6/1994 | Russek | |
| 5,333,106 A | 7/1994 | Lanpher et al. | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| 5,394,877 A | 3/1995 | Orr et al. | |
| 5,406,952 A | 4/1995 | Barnes et al. | |
| D359,546 S | 6/1995 | Savage et al. | |
| 5,428,193 A | 6/1995 | Mandiberg | |
| 5,431,170 A | 7/1995 | Mathews | |
| D361,840 S | 8/1995 | Savage et al. | |
| D362,063 S | 9/1995 | Savage et al. | |
| 5,448,996 A | 9/1995 | Bellin et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,539,831 A | 7/1996 | Harley | |
| 5,561,275 A | 10/1996 | Savage et al. | |
| 5,562,002 A | 10/1996 | Lalin | |
| 5,564,108 A | 10/1996 | Hunsaker et al. | |
| 5,578,799 A | 11/1996 | Callahan et al. | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| 5,730,140 A | 3/1998 | Fitch | |
| D393,830 S | 4/1998 | Tobler et al. | |
| 5,738,106 A | 4/1998 | Yamamori et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,812,678 A | 9/1998 | Scalise et al. | |
| 5,823,950 A | 10/1998 | Diab et al. | |
| 5,825,895 A | 10/1998 | Grasfield et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,912,656 A | 6/1999 | Tham et al. | |
| 5,919,134 A | 7/1999 | Diab | |
| 5,921,941 A | 7/1999 | Longobardo et al. | |
| 5,934,925 A | 8/1999 | Tobler et al. | |
| 5,940,182 A | 8/1999 | Lepper, Jr. et al. | |
| 5,977,538 A | 11/1999 | Unger et al. | |
| 5,987,343 A | 11/1999 | Kinast | |
| 5,989,193 A | 11/1999 | Sullivan | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,048,323 A | 4/2000 | Hon | |
| 6,067,462 A | 5/2000 | Diab et al. | |
| 6,081,735 A | 6/2000 | Diab et al. | |
| 6,083,156 A | 7/2000 | Lisiecki | |
| 6,088,607 A | 7/2000 | Diab et al. | |
| 6,106,481 A | 8/2000 | Cohen | |
| 6,110,522 A | 8/2000 | Lepper, Jr. et al. | |
| 6,124,597 A | 9/2000 | Shehada | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,168,568 B1 | 1/2001 | Gavriely | |
| 6,184,521 B1 | 2/2001 | Coffin, IV et al. | |
| 6,206,830 B1 | 3/2001 | Diab et al. | |
| 6,210,344 B1 | 4/2001 | Perin et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,248,083 B1 | 6/2001 | Smith et al. | |
| 6,253,097 B1 | 6/2001 | Aronow et al. | |
| 6,256,523 B1 | 7/2001 | Diab et al. | |
| 6,261,237 B1 | 7/2001 | Swanson et al. | |
| 6,263,222 B1 | 7/2001 | Diab et al. | |
| 6,271,760 B1 | 8/2001 | Watanabe et al. | |
| 6,275,594 B1 | 8/2001 | Senoo et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,295,365 B1 | 9/2001 | Ota | |
| 6,301,493 B1 | 10/2001 | Marro et al. | |
| 6,308,089 B1 | 10/2001 | von der Ruhr et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,411,014 B1 | 6/2002 | Toda | |
| 6,415,033 B1 | 7/2002 | Halleck et al. | |
| 6,423,013 B1 | 7/2002 | Bakker et al. | |
| 6,430,437 B1 | 8/2002 | Marro | |
| 6,430,525 B1 | 8/2002 | Weber et al. | |

(56) References Cited

U.S. PATENT DOCUMENTS

| | | |
|---|---|---|
| 6,438,238 B1 | 8/2002 | Callahan |
| 6,463,311 B1 | 10/2002 | Diab |
| 6,470,199 B1 | 10/2002 | Kopotic et al. |
| 6,486,588 B2 | 11/2002 | Doron et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,517,497 B2 | 2/2003 | Rymut et al. |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,560,470 B1 * | 5/2003 | Pologe ............... A61B 5/14551 600/310 |
| 6,571,113 B1 | 5/2003 | Fein et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,702,755 B1 | 3/2004 | Stasz et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,074 B1 | 4/2004 | Kästle |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,816,744 B2 | 11/2004 | Garfield et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,937,736 B2 | 8/2005 | Toda |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,954,971 B1 | 10/2005 | Bryant et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,020,508 B2 | 3/2006 | Stivoric et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,035,684 B2 | 4/2006 | Lee |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,096,060 B2 | 8/2006 | Arand et al. |
| 7,110,804 B2 | 9/2006 | Baumer et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,246,069 B1 | 7/2007 | O'Hanlon et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,270,126 B2 | 9/2007 | Wallace et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,361,148 B2 | 4/2008 | Narimatsu |
| 7,368,855 B2 | 5/2008 | Orten |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,469,158 B2 | 12/2008 | Cutler et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |

(56) References Cited

U.S. PATENT DOCUMENTS

| | | |
|---|---|---|
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,515,044 B2 | 4/2009 | Welch et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,625,117 B2 | 12/2009 | Haslett et al. |
| 7,647,083 B2 | 1/2010 | Al-Ali et al. |
| D609,193 S | 2/2010 | Al-Ali et al. |
| 7,662,105 B2 | 2/2010 | Hatlestad |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,783,056 B2 | 8/2010 | Wilmink |
| 7,791,155 B2 | 9/2010 | Diab |
| 7,801,581 B2 | 9/2010 | Diab |
| 7,806,226 B2 | 10/2010 | Drummong et al. |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,860,553 B2 | 12/2010 | Goveri et al. |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,903,825 B1 * | 3/2011 | Melanson .......... H03G 3/32 381/103 |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,940,937 B2 | 5/2011 | Smith |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,976,480 B2 | 7/2011 | Grajales et al. |
| 7,988,637 B2 | 8/2011 | Diab |
| 7,988,688 B2 | 8/2011 | Webb et al. |
| 7,990,382 B2 | 8/2011 | Kiani |
| 7,991,165 B2 | 8/2011 | Kassal et al. |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,092,396 B2 | 1/2012 | Bagha et al. |
| 8,108,039 B2 | 1/2012 | Saliga et al. |
| RE43,169 E | 2/2012 | Parker |
| 8,118,620 B2 | 2/2012 | Al-Ali et al. |
| 8,121,673 B2 | 2/2012 | Tran |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,241,223 B2 | 8/2012 | Gavriely et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,291 B2 | 9/2012 | Bridger et al. |
| 8,265,723 B1 | 9/2012 | McHale et al. |
| 8,274,360 B2 | 9/2012 | Sampath et al. |
| 8,275,140 B2 | 9/2012 | Smith |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| 8,320,576 B1 | 11/2012 | Abbruscato |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,396,228 B2 | 3/2013 | Bilan |
| 8,399,822 B2 | 3/2013 | Al-Ali |
| 8,401,602 B2 | 3/2013 | Kiani |
| 8,403,865 B2 | 3/2013 | Halperin et al. |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,491,489 B2 | 7/2013 | Shin et al. |

(56) References Cited

U.S. PATENT DOCUMENTS

| | | |
|---|---|---|
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,517,981 B2 | 8/2013 | Zornow |
| 8,523,781 B2 | 9/2013 | Al-Ali |
| 8,526,665 B2 | 9/2013 | Lutz et al. |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,595 B2 | 2/2014 | Basinger |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Telfort et al. |
| RE44,875 E | 4/2014 | Kiani et al. |
| 8,688,189 B2 | 4/2014 | Shennib |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,961,413 B2 | 2/2015 | Teller et al. |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |

(56) References Cited

U.S. PATENT DOCUMENTS

| | | |
|---|---|---|
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani et al. |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,955,937 B2 | 5/2018 | Telfort et al. |
| 10,098,610 B2 | 10/2018 | Al-Ali et al. |
| 2002/0193670 A1 | 12/2002 | Garfield et al. |
| 2003/0015368 A1 | 1/2003 | Cybulski et al. |
| 2003/0135087 A1 | 7/2003 | Hickle et al. |
| 2003/0149349 A1 | 8/2003 | Jensen |
| 2003/0196660 A1 | 10/2003 | Haveri |
| 2004/0133087 A1 | 7/2004 | Ali et al. |
| 2004/0158162 A1 | 8/2004 | Narimatsu |
| 2004/0167416 A1 | 8/2004 | Lee |
| 2004/0215094 A1 | 10/2004 | Baumer et al. |
| 2004/0228494 A1 | 11/2004 | Smith |
| 2005/0033128 A1 | 2/2005 | Ali |
| 2005/0065417 A1 | 3/2005 | Ali |
| 2006/0047215 A1 | 3/2006 | Newman et al. |
| 2006/0059324 A1* | 3/2006 | Simske ............ A61B 5/04325 711/170 |
| 2006/0094943 A1 | 5/2006 | Van Slyke |
| 2006/0161054 A1 | 7/2006 | Reuss et al. |
| 2006/0184052 A1 | 8/2006 | Iwasawa |
| 2006/0190051 A1 | 8/2006 | Gerber et al. |
| 2006/0198533 A1 | 9/2006 | Wang |
| 2006/0238333 A1 | 10/2006 | Welch et al. |
| 2006/0264767 A1 | 11/2006 | Shennib |
| 2007/0016030 A1 | 1/2007 | Stringer |
| 2007/0049837 A1 | 3/2007 | Shertukde et al. |
| 2007/0056582 A1 | 3/2007 | Wood et al. |
| 2007/0058818 A1 | 3/2007 | Yoshimine |
| 2007/0106179 A1 | 5/2007 | Bagha et al. |
| 2007/0147639 A1* | 6/2007 | Richardson et al. ......... 381/107 |
| 2007/0165872 A1 | 7/2007 | Bridger et al. |
| 2007/0167855 A1 | 7/2007 | Shin et al. |
| 2007/0173730 A1 | 7/2007 | Bikko |
| 2007/0185397 A1 | 8/2007 | Govari et al. |
| 2007/0208262 A1 | 9/2007 | Kovacs |
| 2007/0255153 A1 | 11/2007 | Kumar et al. |
| 2007/0282174 A1 | 12/2007 | Sabatino |
| 2007/0282212 A1 | 12/2007 | Sierra et al. |
| 2007/0282478 A1 | 12/2007 | Al-Ali et al. |
| 2008/0039735 A1 | 2/2008 | Hickerson |
| 2008/0076972 A1 | 3/2008 | Dorogusker et al. |
| 2008/0077026 A1 | 3/2008 | Banet et al. |
| 2008/0077435 A1 | 3/2008 | Muradia |
| 2008/0093157 A1 | 4/2008 | Drummond et al. |
| 2008/0097249 A1 | 4/2008 | Pool et al. |
| 2008/0139953 A1 | 6/2008 | Baker et al. |
| 2008/0143496 A1* | 6/2008 | Linjama ............ G06F 3/016 340/407.1 |
| 2008/0188733 A1 | 8/2008 | Al-Ali et al. |
| 2008/0188760 A1 | 8/2008 | Al-Ali |
| 2008/0219464 A1 | 9/2008 | Smith |
| 2008/0251313 A1 | 10/2008 | Knight et al. |
| 2008/0281219 A1* | 11/2008 | Glickman ............ A61B 7/003 600/533 |
| 2009/0018429 A1 | 1/2009 | Saliga et al. |
| 2009/0076363 A1 | 3/2009 | Bly et al. |
| 2009/0093687 A1 | 4/2009 | Telfort et al. |
| 2009/0170664 A1 | 7/2009 | Shirasaki |
| 2009/0187065 A1* | 7/2009 | Basinger ............ A61N 1/36032 600/25 |
| 2009/0247924 A1 | 10/2009 | Lamego et al. |

(56) References Cited

U.S. PATENT DOCUMENTS

| | | |
|---|---|---|
| 2009/0247984 A1 | 10/2009 | Lamego et al. |
| 2009/0275813 A1 | 11/2009 | Davis |
| 2009/0275844 A1 | 11/2009 | Al-Ali |
| 2009/0299157 A1 | 12/2009 | Telfort et al. |
| 2009/0299742 A1* | 12/2009 | Toman ............... G10L 21/0208 704/233 |
| 2009/0316925 A1 | 12/2009 | Eisenfeld et al. |
| 2010/0004518 A1 | 1/2010 | Vo et al. |
| 2010/0030040 A1 | 2/2010 | Poeze et al. |
| 2010/0069725 A1 | 3/2010 | Al-Ali |
| 2010/0090901 A1 | 4/2010 | Smith et al. |
| 2010/0094096 A1 | 4/2010 | Petruzzelli et al. |
| 2010/0204996 A1* | 8/2010 | Zeng et al. ............... 704/500 |
| 2010/0261979 A1 | 10/2010 | Kiani |
| 2010/0274099 A1 | 10/2010 | Telfort et al. |
| 2010/0305416 A1 | 12/2010 | Bédard et al. |
| 2010/0317936 A1 | 12/2010 | Al-Ali et al. |
| 2011/0001605 A1 | 1/2011 | Kiani et al. |
| 2011/0028802 A1 | 2/2011 | Addison |
| 2011/0034831 A1 | 2/2011 | Christensen et al. |
| 2011/0082711 A1 | 4/2011 | Poeze et al. |
| 2011/0087083 A1 | 4/2011 | Poeze et al. |
| 2011/0105854 A1 | 5/2011 | Kiani et al. |
| 2011/0125060 A1 | 5/2011 | Telfort et al. |
| 2011/0172561 A1 | 7/2011 | Kiani et al. |
| 2011/0172967 A1 | 7/2011 | Al-Ali et al. |
| 2011/0196211 A1 | 8/2011 | Al-Ali |
| 2011/0208015 A1 | 8/2011 | Welch et al. |
| 2011/0209915 A1 | 9/2011 | Fechter et al. |
| 2011/0213212 A1 | 9/2011 | Al-Ali |
| 2011/0213273 A1 | 9/2011 | Telfort et al. |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0279963 A1 | 11/2011 | Kumar et al. |
| 2011/0288383 A1 | 11/2011 | Diab |
| 2011/0288431 A1 | 11/2011 | Alshaer et al. |
| 2011/0301444 A1 | 12/2011 | Al-Ali |
| 2012/0041316 A1 | 2/2012 | Al-Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0116175 A1 | 5/2012 | Al-Ali et al. |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0230523 A1 | 9/2012 | Ehrlund |
| 2012/0232427 A1 | 9/2012 | Bakema et al. |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0302920 A1 | 11/2012 | Bridger et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0338461 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0262730 A1 | 10/2013 | Al-Ali et al. |
| 2013/0267804 A1 | 10/2013 | Al-Ali |
| 2013/0274571 A1 | 10/2013 | Diab et al. |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317327 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0324817 A1 | 12/2013 | Diab |
| 2013/0331660 A1 | 12/2013 | Al-Ali et al. |
| 2013/0331670 A1 | 12/2013 | Kiani |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0303520 A1 | 10/2014 | Telfort et al. |
| 2014/0309506 A1 | 10/2014 | Lamego et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiana |
| 2014/0336481 A1 | 11/2014 | Shakespeare et al. |
| 2014/0343436 A1 | 11/2014 | Kiani |
| 2014/0355966 A1 | 12/2014 | Al-Ali et al. |
| 2014/0371548 A1 | 12/2014 | Al-Ali et al. |

(56) References Cited

U.S. PATENT DOCUMENTS

| | | |
|---|---|---|
| 2014/0371632 A1 | 12/2014 | Al-Ali et al. |
| 2014/0378784 A1 | 12/2014 | Kiani et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0099998 A1 | 4/2015 | Christensen et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224231 A1 | 8/2017 | Al-Ali |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0110478 A1 | 4/2018 | Al-Ali |
| 2018/0125445 A1 | 5/2018 | Telfort et al. |
| 2018/0153446 A1 | 6/2018 | Kiani |
| 2018/0206815 A1 | 7/2018 | Telfort |
| 2018/0289337 A1 | 10/2018 | Al-Ali et al. |

FOREIGN PATENT DOCUMENTS

| | | |
|---|---|---|
| CN | 201497610 | 6/2010 |
| CN | 202005761 | 10/2011 |
| EP | 0716628 | 12/1998 |
| EP | 0659058 | 1/1999 |
| EP | 0956820 A1 | 11/1999 |
| EP | 1207536 | 5/2002 |
| EP | 1518442 | 3/2005 |
| EP | 2 014 234 | 1/2009 |
| EP | 1207536 | 2/2010 |
| EP | 2391273 | 12/2011 |
| EP | 2488106 | 8/2012 |
| EP | 2488978 | 8/2012 |
| EP | 2710959 | 3/2014 |
| FR | 2 847 796 | 6/2004 |
| GB | 2358546 | 11/1999 |
| GB | 2358546 | 7/2001 |
| JP | S56-031742 A | 3/1961 |
| JP | S53-094482 A | 8/1978 |
| JP | 60059900 | 4/1985 |
| JP | 6214898 | 1/1987 |
| JP | 01-309872 | 12/1989 |

(56) References Cited

FOREIGN PATENT DOCUMENTS

| JP | H04-317637 A | 11/1992 |
|---|---|---|
| JP | H07-152553 A | 6/1995 |
| JP | 01-309872 | 6/1998 |
| JP | 10-155755 | 6/1998 |
| JP | 2001-50713 | 5/1999 |
| JP | 2001-50713 | 2/2001 |
| JP | 2003-329719 | 11/2003 |
| JP | 2005-522292 A | 7/2005 |
| JP | 2005-531230 A | 10/2005 |
| JP | 2012-513872 | 6/2012 |
| JP | 2013-508029 | 3/2013 |
| JP | 2013-508030 | 3/2013 |
| NO | 20040819 | 2/2004 |
| WO | WO 1994/005207 | 3/1994 |
| WO | WO 1994/013207 | 6/1994 |
| WO | WO 1995/029632 | 11/1995 |
| WO | WO 1999/053277 | 10/1999 |
| WO | WO 2000/010462 | 3/2000 |
| WO | WO 2001/034033 | 5/2001 |
| WO | WO 2001/078059 | 10/2001 |
| WO | WO 2001/87005 | 11/2001 |
| WO | WO 2001/097691 | 12/2001 |
| WO | WO 2002/003042 | 1/2002 |
| WO | WO 2001/078059 | 3/2002 |
| WO | WO 2002/024067 | 7/2002 |
| WO | WO 2002/003042 | 12/2002 |
| WO | WO 2003/058646 | 7/2003 |
| WO | WO 2003/087737 | 10/2003 |
| WO | WO 2004/000111 | 12/2003 |
| WO | WO 2004/004411 | 1/2004 |
| WO | WO 2004/078038 | 9/2004 |
| WO | WO 2005/096931 | 10/2005 |
| WO | WO 2005/099562 | 10/2005 |
| WO | WO 2008/017246 | 2/2008 |
| WO | WO 2008/148172 | 12/2008 |
| WO | WO 2009/137524 | 11/2009 |
| WO | WO 2009/155593 | 12/2009 |
| WO | WO 2010/078168 | 7/2010 |
| WO | WO 2011/047207 | 4/2011 |
| WO | WO 2011/047209 | 4/2011 |
| WO | WO 2011/047213 | 4/2011 |
| WO | WO 2011/047216 | 4/2011 |
| WO | WO 2011/0147211 | 4/2011 |
| WO | WO 2011/047207 | 9/2011 |
| WO | WO 2011/047209 | 3/2012 |
| WO | WO 2013/056141 | 4/2013 |

OTHER PUBLICATIONS

US 8,845,543 B2, 09/2014, Diab et al. (withdrawn)
P. White, "Advanced Compression Techniques, Tips & Tricks", Part 1 and Part 2 (White).*
Eldor et al., "A device for monitoring ventilation during anaesthesia; the paratracheal audible respiratory monitor", Canadian Journal of Anaesthesia, 1990, vol. 9, No. 1, p. 95-98.
U.S. Appl. No. 12/904,775, filed Oct. 14, 2010, Fetcher et al.
U.S. Appl. No. 12/904,823, filed Oct. 14, 2010, Al-Ali et al.
U.S. Appl. No. 12/904,836, filed Oct. 14, 2010, Al-Ali, Ammar.
U.S. Appl. No. 12/904,890, filed Oct. 14, 2010, Telfort et al.
U.S. Appl. No. 12/904,907, filed Oct. 14, 2010, Telfort et al.
U.S. Appl. No. 12/904,931, filed Oct. 14, 2010, Telfort et al.
U.S. Appl. No. 12/904,938, filed Oct. 14, 2010, Telfort et al.
U.S. Appl. No. 12/905,036, filed Oct. 14, 2010, Kiani et al.
U.S. Appl. No. 12/905,384, filed Oct. 15, 2010, Al-Ali et al.
U.S. Appl. No. 12/905,449, filed Oct. 15, 2010, Al-Ali et al.
U.S. Appl. No. 12/905,489, filed Oct. 15, 2010, Weber et al.
U.S. Appl. No. 12/905,530, filed Oct. 15, 2010, Al-Ali et al.
U.S. Appl. No. 12/960,325, filed Dec. 3, 2010, Al-Ali, Ammar et al.
International Search Report, PCT Application PCT/US2009/069287, dated Mar. 30, 2010; 7 pages.
Welch Allyn, ECG ASIC, Product Data Sheete, 2001.
Sierra et al., Monitoring Respiratory Rate Based on Tracheal Sounds. First Experieances, Proceedings of the 26th Annual Int'l Conf. of the IEEE EMBS (Sep. 2004), 317-320.

Internationl Search Report and Written Opinion in PCTUS2010052760 dated Mar. 8, 2011—in 11 pages.
Sierra, G., et al.: "Monitoring Respiratory Rate Based on Tracheal Sounds. First Experiences", Proceedings of the 26th Annual International Conference of the IEEE EMBS, Sep. 2004, pp. 317-320.
Avago Technologies, "HCNR200 and HCNR201, High-Linearity Analog Optocouplers," Data Sheet, Avago Technologies, Nov. 18, 2008.
Images showing tear down of a Measurement Specialties' stethoscope, Images taken on Sep. 7, 2007, in 38 pages.
Oversampling by Wikipedia, the free encyclopedia, pub. Online Oct. 7, 2012 at "https://wikipedia.org/w/index.php?title=Oversampling &oldid=516454012", accessed Sep. 3, 2015.
Pseudorandom noise by Wikipedia, the free encyclopedia, pub. Online Jul. 25, 2012 at "https://wikipedia.org/w/index.php?title= Pseudorandom_noise&oldid=504121479", accessed Sep. 3, 2015.
Noise generator by Wikipedia, the free encyclopedia, pub. Online May 6, 2012 at "https://wikipedia.org/w/index.php?title=Noise_ generator&oldid=490897729", accessed Sep. 3, 2015.
International Search Report and Written Opinion for PCT/US2009/ 042902, dated Dec. 8, 2009.
International Search Report and Written Opinion in PCT/US2009/ 042902 dated Aug. 12, 2009 in 16 pages.
EP Office Action dated May 18, 2011 in application No. 03711767.8.
PCT Invitation to Pay Fees and Initial Search Report in PCT/ US2010/052756, dated Oct. 5, 2011.
International Search Report and Written Opinion in PCT/US2010/ 052756 dated Feb. 6, 2012 in 14 pages.
PCT Invitation to Pay Fees and Initial Search Report in PCT/ US2009/069287, dated Apr. 21, 2010.
International Search Report and Written Opinion issued in PCT Application No. PCT/US2009/069287, dated Jun. 30, 2010.
Office Action in Japanese Application No. 2011-544508 dated Apr. 30, 2014.
EP Office Action dated Mar. 5, 2013 in application No. 10779086.7.
EP Office Action dated Jul. 11, 2016 in application No. 10779086.7.
EP Office Action dated May 12, 2017 in application No. 10779086.7.
International Search Report and Written Opinion in PCT/US2010/ 052754 dated Jul. 27, 2011.
International Preliminary Report on Patentability (IPRP) in PCT/ US2010/052754 dated Apr. 26, 2012 in 11 pages.
International Preliminary Report on Patentability in PCT/US2010/ 052763 dated Apr. 17, 2012 in 9 pages.
International Search Report and Written Opinion in PCT Application No. PCT/US2012/060084 dated Dec. 21, 2012 in 11 pages.
International Preliminary Report on Patentability dated Apr. 15, 2014 for PCT Application No. PCT/US2012/060084.
European Search Report for Application No. 13185148.7 dated Dec. 6, 2013.
Office Action for Application No. 13185148.7 dated Apr. 4, 2017.
Office Action for Application No. 13185148.7 dated Nov. 7, 2017.
Analog Devices, 12-Bit Serial Input Multiplying D/A Converter, Product Data Sheet, 2000.
Eldor et al., "A device for monitoring ventilation during anesthesia; the paratracheal audible respiratory monitor", Canadian Journal of Anesthesia, 1990, vol. 9, No. 1, p. 95-98.
Sierra et al., Monitoring Respiratory Rate Based on Tracheal Sounds. First Experiences, Proceedings of the 26th Annual Int'l Conf. of the IEEE EMBS (Sep. 2004), 317-320.
WelchAllyn OEM Technologies, ECG ASIC, ECG 3-lead, 5-lead, 12-lead and RESP Signal Processing, ECG ASIC Part No. 000. 91163 (2001).
International Search Report & Written Opinion, PCT Application PCT/US2010/052758, dated Feb. 10, 2011; 12 pages.
International Search Report & Written Opinion, PCT Application PCT/US2010/058981, dated Feb. 17, 2011; 11 pages.
International Search Report, PCT Application PCT/CA2003/ 000536, dated Dec. 11, 2003; 2 pages.
Japanese Office Action re Application No. 2007-506626, dated Mar. 1, 2011.

(56) References Cited

OTHER PUBLICATIONS

International Search Report & Written Opinion for PCT/US2010/052756, dated Feb. 6, 2012; 17 pages.
EP Office Action dated Oct. 16, 2018 in application No. 10773191.1.
EP Office Action dated Dec. 10, 2018 in application No. 10779086.7.
PCT Invitation to Pay Fees and Initial Search Report in PCT/US2010/052754, dated Mar. 15, 2011.
International Search Report and Written Opinion in PCTUS2010052760 dated Mar. 8, 2011 in 11 pages.
International Search Report and Written Opinion in PCT/US2010/052763, dated May 13, 2011.
Office Action in European Application No. 12784142.7 dated Apr. 10, 2018 in 5 pages.

\* cited by examiner

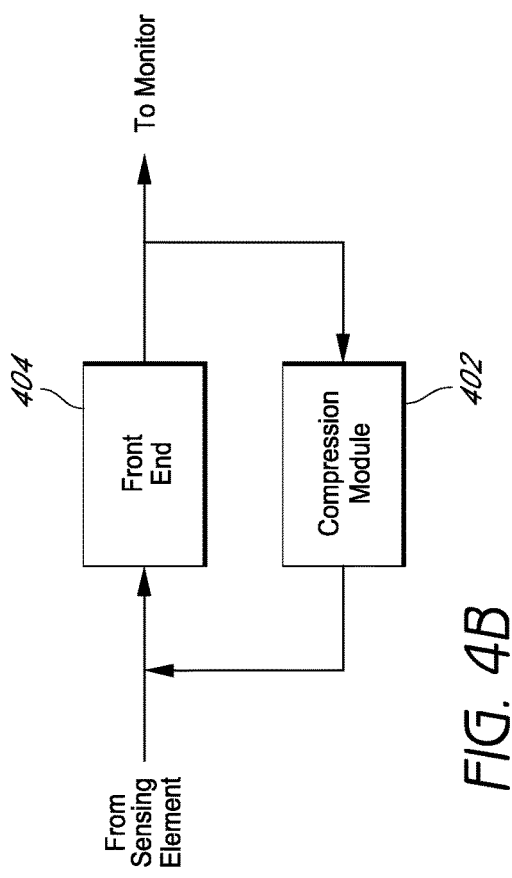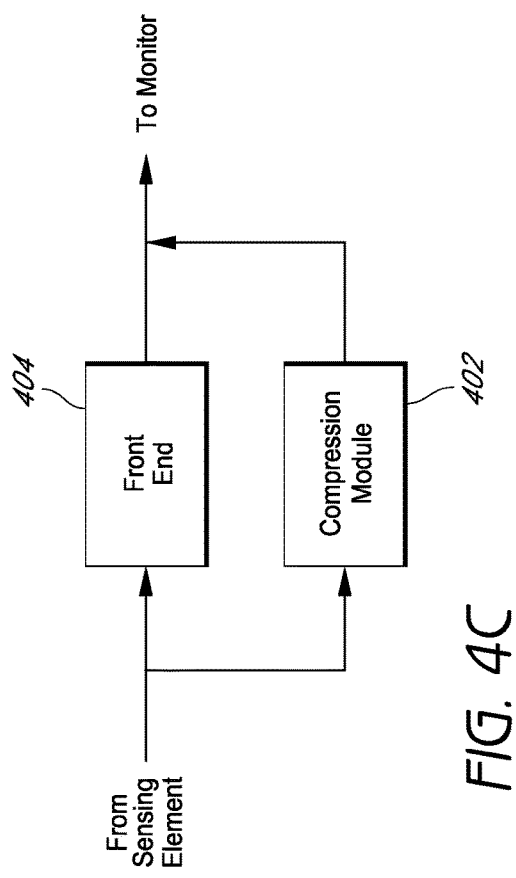

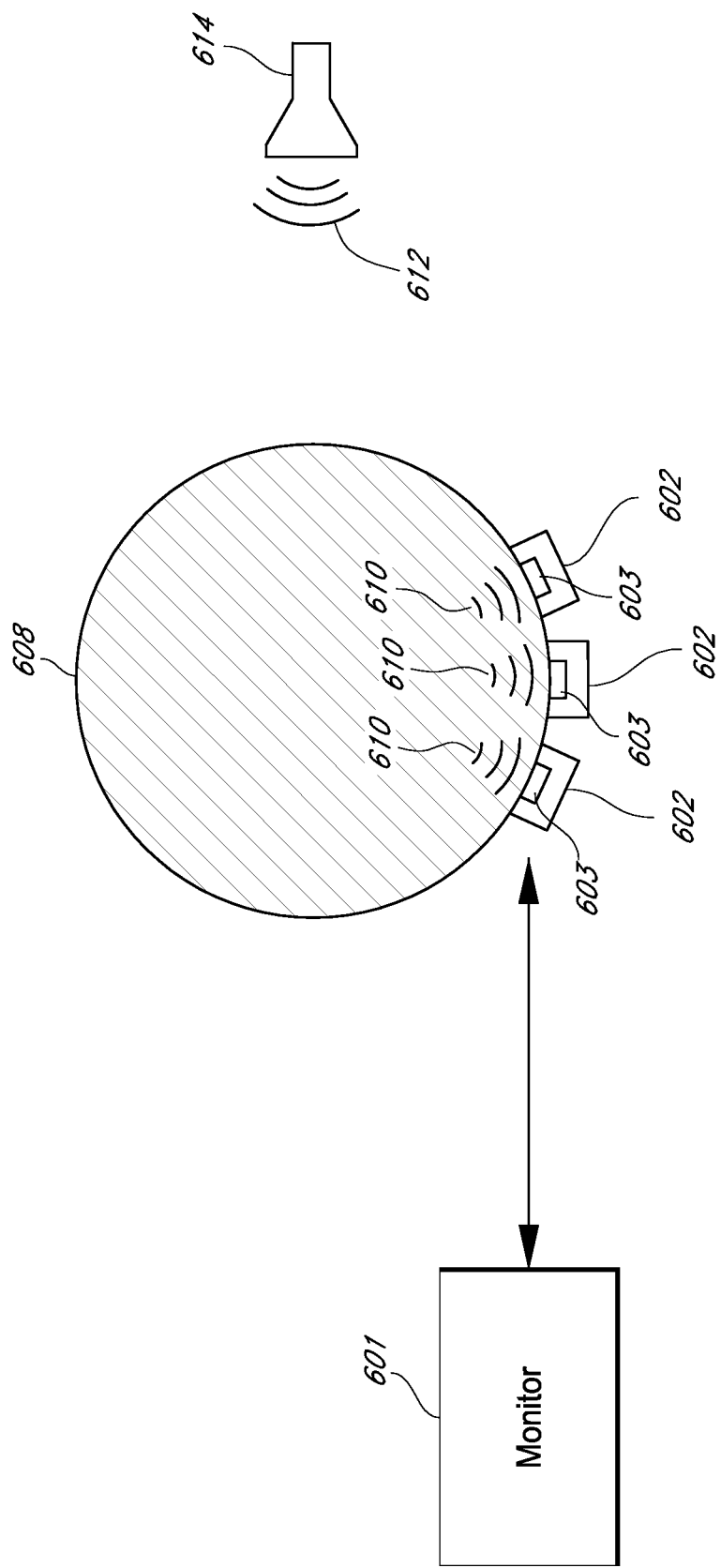

ACOUSTIC RESPIRATORY MONITORING SYSTEMS AND METHODS

CROSS-REFERENCE TO RELATED APPLICATIONS

This application claims the benefit of priority under 35 U.S.C. § 119(e) of U.S. Provisional Application No. 61/252,099, filed Oct. 15, 2009, the disclosure of which is incorporated in its entirety by reference herein.

Additionally, this application relates to the following U.S. patent applications, the disclosures of which are incorporated in their entirety by reference herein:

| Application Ser. No. | Filing Date | Title |
| --- | --- | --- |
| 60/893,853 | Mar. 08, 2007 | MULTI-PARAMETER PHYSIOLOGICAL MONITOR |
| 60/893,850 | Mar. 08, 2007 | BACKWARD COMPATIBLE PHYSIOLOGICAL SENSOR WITH INFORMATION ELEMENT |
| 60/893,858 | Mar. 08, 2007 | MULTI-PARAMETER SENSOR FOR PHYSIOLOGICAL MONITORING |
| 60/893,856 | Mar. 08, 2007 | PHYSIOLOGICAL MONITOR WITH FAST GAIN ADJUST DATA ACQUISITION |
| 12/044,883 | Mar. 08, 2008 | SYSTEMS AND METHODS FOR DETERMINING A PHYSIOLOGICAL CONDITION USING AN ACOUSTIC MONITOR |
| 61/252,083 | Oct. 15, 2009 | DISPLAYING PHYSIOLOGICAL INFORMATION |
| 12/904,836 | Oct. 14, 2010 | BIDIRECTIONAL PHYSIOLOGICAL INFORMATION DISPLAY |
| 12/904,823 | Oct. 14, 2010 | BIDIRECTIONAL PHYSIOLOGICAL INFORMATION DISPLAY |
| 61/141,584 | Dec. 30, 2008 | ACOUSTIC SENSOR ASSEMBLY |
| 61/252,076 | Oct. 15, 2009 | ACOUSTIC SENSOR ASSEMBLY |
| 12/643,939 | Dec. 21, 2009 | ACOUSTIC SENSOR ASSEMBLY |
| 61/313,645 | Mar. 12, 2010 | ACOUSTIC RESPIRATORY MONITORING SENSOR HAVING MULTIPLE SENSING ELEMENTS |
| 12/904,931 | Oct. 14, 2010 | ACOUSTIC RESPIRATORY MONITORING SENSOR HAVING MULTIPLE SENSING ELEMENTS |
| 12/904,890 | Oct. 14, 2010 | ACOUSTIC RESPIRATORY MONITORING SENSOR HAVING MULTIPLE SENSING ELEMENTS |
| 12/904,938 | Oct. 14, 2010 | ACOUSTIC RESPIRATORY MONITORING SENSOR HAVING MULTIPLE SENSING ELEMENTS |
| 12/904,907 | Oct. 14, 2010 | ACOUSTIC PATIENT SENSOR |
| 61/252,062 | Oct. 15, 2009 | PULSE OXIMETRY SYSTEM WITH LOW NOISE CABLE HUB |
| 61/265,730 | Dec. 01, 2009 | PULSE OXIMETRY SYSTEM WITH ACOUSTIC SENSOR |
| 12/904,775 | Oct. 14, 2010 | PULSE OXIMETRY SYSTEM WITH LOW NOISE CABLE HUB |
| 12/904,036 | Oct. 14, 2010 | PHYSIOLOGICAL ACOUSTIC MONITORING SYSTEM |
| 61/331,087 | May 04, 2010 | ACOUSTIC RESPIRATION DISPLAY |
| 61/391,098 | Oct. 08, 2010 | ACOUSTIC MONITOR |

Many of the embodiments described herein are compatible with embodiments described in the above related applications. Moreover, some or all of the features described herein can be used or otherwise combined with many of the features described in the applications listed above.

BACKGROUND

Field

The present disclosure relates to non-invasive biological parameter sensing, including sensing using acoustic sensors and related systems and methods.

Description of the Related Art

The "piezoelectric effect" is the appearance of an electric potential and current across certain faces of a crystal when it is subjected to mechanical stresses. Due to their capacity to convert mechanical deformation into an electric voltage, piezoelectric crystals have been broadly used in devices such as transducers, strain gauges and microphones. However, before the crystals can be used in many of these applications they must be rendered into a form which suits the requirements of the application. In many applications, especially those involving the conversion of acoustic waves into a corresponding electric signal, piezoelectric membranes have been used.

Piezoelectric membranes are typically manufactured from polyvinylidene fluoride plastic film. The film is endowed with piezoelectric properties by stretching the plastic while it is placed under a high-poling voltage. By stretching the film, the film is polarized and the molecular structure of the plastic aligned. A thin layer of conductive metal (typically nickel-copper) is deposited on each side of the film to form electrode coatings to which connectors can be attached.

Piezoelectric membranes have a number of attributes that make them interesting for use in sound detection, including: a wide frequency range of between 0.001 Hz to 1 GHz; a low acoustical impedance close to water and human tissue; a high dielectric strength; a good mechanical strength; and piezoelectric membranes are moisture resistant and inert to many chemicals.

Due in large part to the above attributes, piezoelectric membranes are particularly suited for the capture of acoustic waves and the conversion thereof into electric signals and, accordingly, have found application in the detection of body sounds. However, there is still a need for reliable acoustic respiratory monitoring systems.

SUMMARY

There are often a wide variety of types and intensities of sounds present in a physiological monitoring environment. Thus, it is often desirable to accurately process a wide range of physiological sounds. For example, in many circumstances, medical personnel would benefit from the ability to monitor, record and/or reproduce physiological sounds ranging from relatively low intensity to relatively high intensity physiological sounds.

According to certain aspects described herein, an acoustic sensor is configured to accurately capture a wide range of physiological sound content. Such sounds can include a relatively wide range of physiological sounds, including relatively quiet sounds such as breath, soft speech, heart sounds, etc., as well as relatively loud sounds such as loud speech, coughing, gasping, and the like.

To achieve these and other benefits, componentry in the sensor data path generally compresses, reduces, or otherwise modifies a signal output by a sensing element or other component, improving the overall dynamic range of the sensor. For example, a piezoelectric film or other sensing element may have a relatively high input dynamic range, and may therefore be capable of generating a signal representing a wide range of sound intensity values. The sensing element may also have a relatively high output dynamic range and thus have a large range of possible output signal values (e.g., voltage values). However, one or more subsequent components in the sensor data path, such as a preamplifier or other circuit, may have a relatively lower input dynamic range, and thus be capable of processing a range of input signal values that is significantly smaller than the range of values produced by the sensing element.

If the unmodified signal from the sensing element is provided to the preamplifier, the preamplifier may saturate or otherwise produce a distorted output for signal values received by the sensing element that are above a threshold value (e.g., saturation threshold). This can result in a loss of sound content, and a corresponding reduction in the overall dynamic range of the sensor. To mitigate such losses, certain techniques described herein compress or otherwise modify the signal produced by the sensing element, and provide the compressed signal to the preamplifier or other subsequent sensor stage. The signal is compressed sufficiently to prevent saturation at the preamplifier for a desired range of signal values, thereby improving the overall dynamic range of the sensor. For example, the signal may be compressed based on the input dynamic range of the preamplifier or other relatively low dynamic range component. In additional embodiments, the output of the lower dynamic range component (e.g., preamplifier or other component) is compressed directly instead of, or in addition to, compressing the sensing element output.

Additionally, while compression can have distortive effects on the sound signal, such distortions can be advantageously removed or reduced according to certain aspects by performing a decompression operation. Such an operation can be performed before providing the signal for output for display, for the processing of physiological characteristics, and the like.

As will be described, acoustic sensors and systems provided herein, such as those having the above-described capabilities and/or other capabilities described herein, can be suited for a variety of beneficial applications, including enhanced physiological monitoring, sound processing, audio communication, identification and handling of medical emergencies, and the like.

An acoustic sensor is provided according to certain aspects for non-invasively detecting physiological acoustic vibrations indicative of one or more physiological parameters of a medical patient. The sensor can include an acoustic sensing element configured to generate a first signal in response to acoustic vibrations from a medical patient. The sensor can also include front-end circuitry configured to receive an input signal that is based at least in part on the first signal and to produce an amplified signal in response to the input signal. In some embodiments, the sensor further includes a compression module in communication with the front-end circuitry and configured to compress portions of at least one of the input signal and the amplified signal according to a first compression scheme, the compressed portions corresponding to portions of the first signal having a magnitude greater than a predetermined threshold level.

In certain embodiments, an acoustic sensor is provided for non-invasively detecting physiological acoustic vibrations indicative of one or more physiological parameters of a medical patient. The acoustic sensor can include a sensing element configured to generate an output signal in response to acoustic vibrations from a medical patient. The acoustic sensing element according to certain embodiments has an output dynamic range. The front-end circuitry can be in communication with the acoustic sensing element and have a dynamic range. In some embodiments, the dynamic range of the front-end circuitry is less than the output dynamic range of the acoustic sensing element. The sensor can further include a dynamic range module configured, in response to the output signal, to maintain the output signal's intensity within the dynamic range of the front-end circuitry.

In certain embodiments, a method is provided for increasing the dynamic range of a sensor capable of non-invasively detecting physiological acoustic vibrations indicative of one or more physiological parameters of a medical patient, comprising. The method can include outputting a first signal using a first sensing element and in response to acoustic vibrations from a medical patient. The method can also include generating an amplified signal using front-end circuitry and in response an input signal that is based at least in part on the first signal. In certain embodiments, the method also includes compressing portions of at least one of the input signal and the amplified signal according to a first compression scheme. The compressed portions may correspond to portions of the first signal having a magnitude greater than a predetermined threshold level, for example.

In certain embodiments, a method of improving the dynamic range of an acoustic respiratory monitoring system is provided. The method includes providing an acoustic sensor comprising a sensing element configured to detect acoustic vibrations at a measurement site of a medical patient. The method further includes receiving a signal indicative of acoustic vibrations from the acoustic sensor. The method also includes compressing the signal to avoid saturation when the signal amplitude exceeds a predetermined threshold.

An acoustic respiratory monitor is provided including an acoustic sensor input configured to receive a signal indicative of acoustic vibrations from an acoustic sensor attached to a measurement site of a medical patient. The respiratory monitor also includes a compression module configured to compress the signal to avoid saturation when the signal amplitude exceeds a predetermined threshold.

A method of non-invasively sensing one or more physiological parameters of a medical patient is provided. The method includes providing a plurality of acoustic sensors each comprising a sensing element configured to detect acoustic vibrations, each of the plurality of acoustic sensors configured to attach to a corresponding measurement site on a medical patient. The method further includes receiving a plurality of signals indicative of acoustic vibrations detected by the plurality of acoustic sensors, each of the plurality of signals comprising a physiological signal component and a noise component. The method of certain embodiments also includes processing the plurality of signals to generate a reduced noise signal indicative of a physiological parameter of the medical patient. The reduced noise signal can have a higher signal-to-noise ratio than any of the plurality of signals. The processing can comprise performing a cross-correlation using the plurality of signals. The processing can also include a shift-and-add operation using the plurality of signals. The processing in some embodiments comprises locating a point of maximum energy between two of the signals. The processing in yet additional embodiments comprises shifting one or more of the plurality of signals with respect to one or more of the other signals so that the physiological components of the signals are substantially in phase with respect to one another. The processing can include combining the plurality of signals together after the shifting. The noise components of the plurality of signals are substantially out of phase with respect to one another after the shifting in some embodiments.

A system for non-invasively sensing one or more physiological parameters of a medical patient is provided. The system includes a plurality of acoustic sensors each comprising a sensing element configured to detect acoustic vibrations. The plurality of acoustic sensors are configured to be attached to a corresponding plurality of measurement sites on a medical patient. The system further includes a processor configured to receive a signal from each of said acoustic sensors, each signal having a physiological signal component and a noise component. Each signal is further indicative of acoustic vibrations detected by the plurality of acoustic sensors. The processor is also configured to process the signals to generate a reduced noise signal indicative of a physiological parameter of the medical patient. In some embodiments, the reduced noise signal has a higher signal-to-noise ratio than any of the plurality of signals. In some embodiments, processor is further configured to perform a cross-correlation using the plurality of signals. In some embodiments, the processor is further configured to perform a shift-and-add operation using the plurality of signals. In embodiments, the processor is further configured to determine a point of maximum energy between two of the signals. The processor can be configured to: shift one or more of the plurality of signals with respect to one or more of the other signals such that the physiological components of the signals are substantially in phase with respect to one another; and combine the plurality of signals together after the shifting. Moreover, the noise components of the plurality of signals are substantially out of phase with respect to one another after the shifting in some embodiments. In some embodiments, the plurality of acoustic sensors are connected together via at least one monitor cable.

In certain embodiments, a method of determining a tissue characterization parameter of tissue at a measurement site using an active acoustic sensor of an acoustic respiratory monitoring system is provided. The method includes providing an acoustic sensor comprising a sensing element configured to transmit and detect acoustic vibrations. The method further includes transmitting first acoustic vibrations into a measurement site of a medical patient with the sensor. The method also includes detecting second acoustic vibrations with the acoustic sensor, the detected second acoustic vibrations being generated at least in part in response to the transmitted first acoustic vibration. In certain embodiments, the method also includes processing a signal indicative of the detected second acoustic vibrations to determine a tissue characterization parameter. In certain embodiments, the tissue characterization parameter indicates integrity of a mechanical connection between the acoustic sensor and the measurement site. In some embodiments, the tissue characterization parameter is a probe-off condition. In yet other embodiments, the tissue characterization parameter indicates a tissue type. In some embodiments, the tissue characterization parameter indicates a tissue composition. The processing can further comprise removing noise from the signal based on the detected second acoustic vibrations.

An acoustic respiratory monitor configured to determine a tissue characterization parameter at a tissue measurement site using an active acoustic sensor, the acoustic respiratory monitor is provided in certain embodiments. The monitor includes an active acoustic sensor port configured for attachment with an active acoustic sensor coupled to a measurement site of a medical patient. In certain embodiments, the active acoustic sensor has a sensing element configured to transmit and detect acoustic vibrations. The monitor further includes a processor configured to transmit a first signal to the active sensor port, the transmitted first signal configured to cause the active acoustic sensor to transmit a first acoustic vibration to the measurement site. The processor is also configured to receive a second signal from the active sensor port, the received second signal indicative of acoustic vibrations detected by the active acoustic sensor. The process may also be configured to process the received second signal indicative of the detected acoustic vibrations to determine a tissue characterization parameter. In certain embodiments, the sensing element comprises a single piezoelectric membrane. The sensing element can comprise a first piezoelectric membrane configured to transmit acoustic vibrations and a second piezoelectric member configured to detect acoustic vibrations. In some embodiments, tissue characterization parameter indicates integrity of a mechanical connection between the acoustic sensor and the measurement site.

A method of generating an auscultatory output with an acoustic respiratory monitor is provided in certain embodiments. The method comprises providing an acoustic respiratory monitor configured to receive a signal indicative of a physiological parameter of a medical patient from an acoustic sensor attached to the medical patient. The method also includes generating an output signal corresponding to the physiological parameter, the output signal being audible to a clinician when provided to an acoustic transducer. The method also includes providing the output signal to the clinician via a communication link. The acoustic sensor can include piezoelectric membrane. In some embodiments, the communication link comprises a wireless communication link. The providing can comprises providing the output signal to the connection over the Internet, for example.

An acoustic respiratory monitor configured to provide an auscultatory output to remote location is provided in certain embodiments. The monitor includes an acoustic sensor input configured to receive a signal indicative of a physiological parameter of a medical patient from an acoustic sensor attached to the medical patient. The monitor also includes a processor configured to generate an output signal corresponding to the physiological parameter, the output signal being audible to a clinician when provided to an acoustic transducer. The method further includes a communication module, configured to communicate the output signal to the clinician via a communication link. In certain embodiments, the acoustic sensor comprises a piezoelectric membrane. The communication module can comprise a wireless transmitter. The communication module can also be configured to communicate to the clinician over the Internet.

BRIEF DESCRIPTION OF THE DRAWINGS

FIGS. 4B and 4C are schematic diagrams illustrating additional dynamic range compression architectures according to certain embodiments.

FIGS. 6A-B are top views of embodiments in which a plurality of sensors are attached to a patient according to embodiments of the disclosure.

DETAILED DESCRIPTION

Various embodiments will be described hereinafter with reference to the accompanying drawings. These embodiments are illustrated and described by example only, and are not intended to be limiting.

System Overview

In various embodiments, an acoustic sensor configured to operate with a physiological monitoring system includes an acoustic signal processing system that measures and/or determines any of a variety of physiological parameters of a medical patient. For example, in one embodiment, the physiological monitoring system includes an acoustic monitor. The acoustic monitor may be an acoustic respiratory monitor which can determine any of a variety of respiratory parameters of a patient, including respiratory rate, expiratory flow, tidal volume, minute volume, apnea duration, breath sounds, riles, rhonchi, stridor, and changes in breath sounds such as decreased volume or change in airflow. In addition, in some cases the acoustic signal processing system monitors other physiological sounds, such as heart rate which can be used to determine a probe off condition, heart sounds (S1, S2, S3, S4, and murmurs, etc.), and change in heart sounds such as normal to murmur or split heart sounds indicating fluid overload.

Moreover, the acoustic signal processing system may: (1) use one or more additional probes to detect additional heart sounds; (2) keep the user inputs to a minimum (example, height); and/or (3) use a Health Level 7 (HL7) interface to automatically input patient demography.

In certain embodiments, the physiological monitoring system includes an electrocardiograph (ECG or EKG) that measures and/or determines electrical signals generated by the cardiac system of a patient. The ECG includes one or more sensors for measuring the electrical signals. In some embodiments, the electrical signals are obtained using the same sensors used to obtain acoustic signals.

In still other embodiments, the physiological monitoring system includes one or more additional sensors used to determine other desired physiological parameters. For example, in some embodiments, a photoplethysmograph sensor determines the concentrations of analytes contained in the patient's blood, such as oxyhemoglobin, carboxyhemoglobin, methemoglobin, other dyshemoglobins, total hemoglobin, fractional oxygen saturation, glucose, bilirubin, and/or other analytes. In other embodiments, a capnograph determines the carbon dioxide content in inspired and expired air from a patient. In other embodiments, other sensors determine blood pressure, pressure sensors, flow rate, air flow, and fluid flow (first derivative of pressure). Other sensors may include a pneumotachometer for measuring air flow and a respiratory effort belt. In certain embodiments, these sensors are combined in a single processing system which processes signal output from the sensors on a single multi-function circuit board.

Figure 4A:
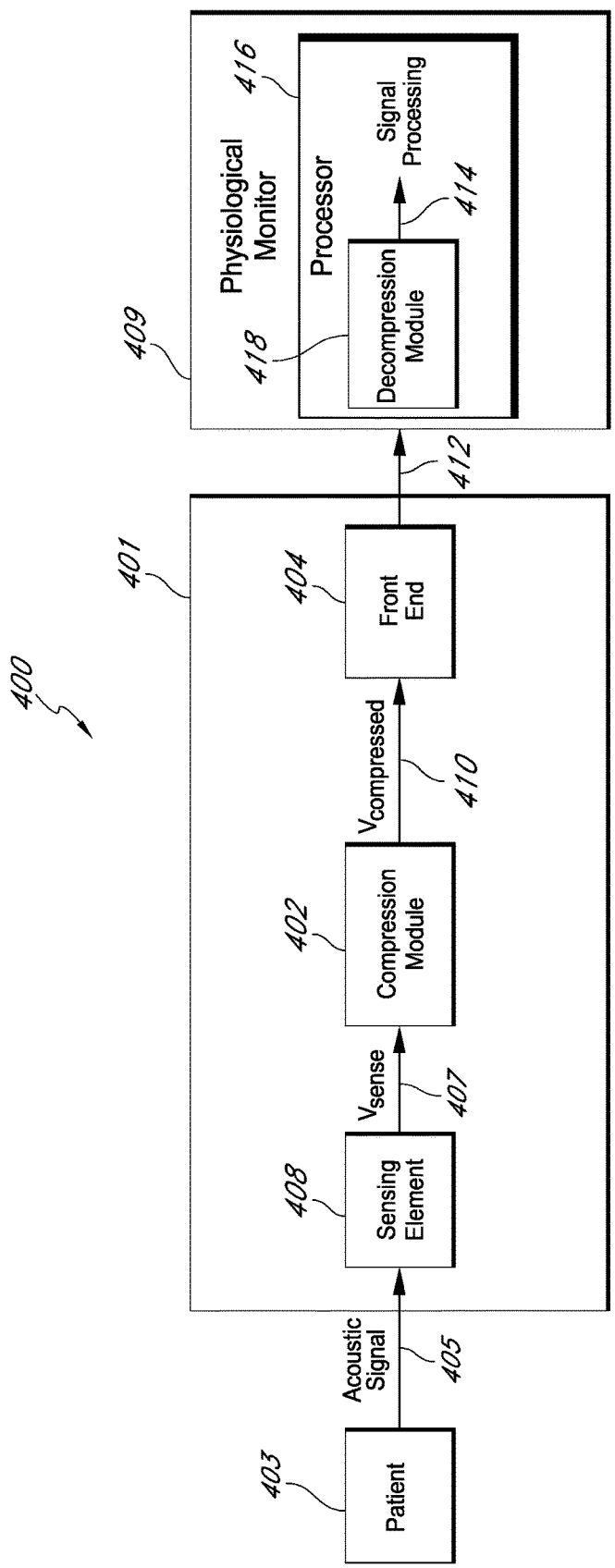
FIG. 4A is a schematic diagram of one embodiment of a system including a sensor configured to perform dynamic range compression.
Figure 4D:
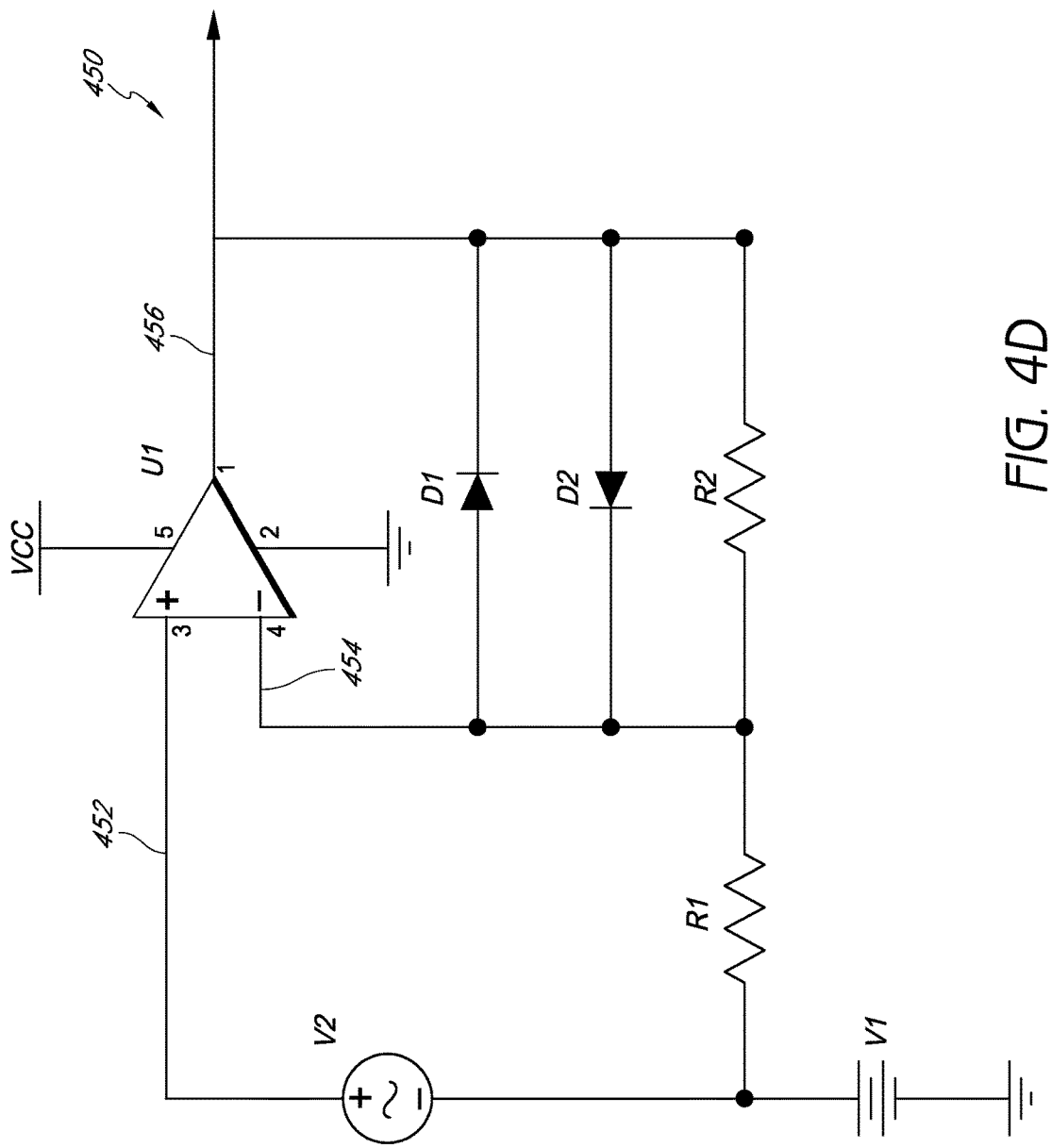
FIG. 4D illustrates a diagram of an example circuit configured to perform dynamic range compression according to one embodiment.
Figure 5:
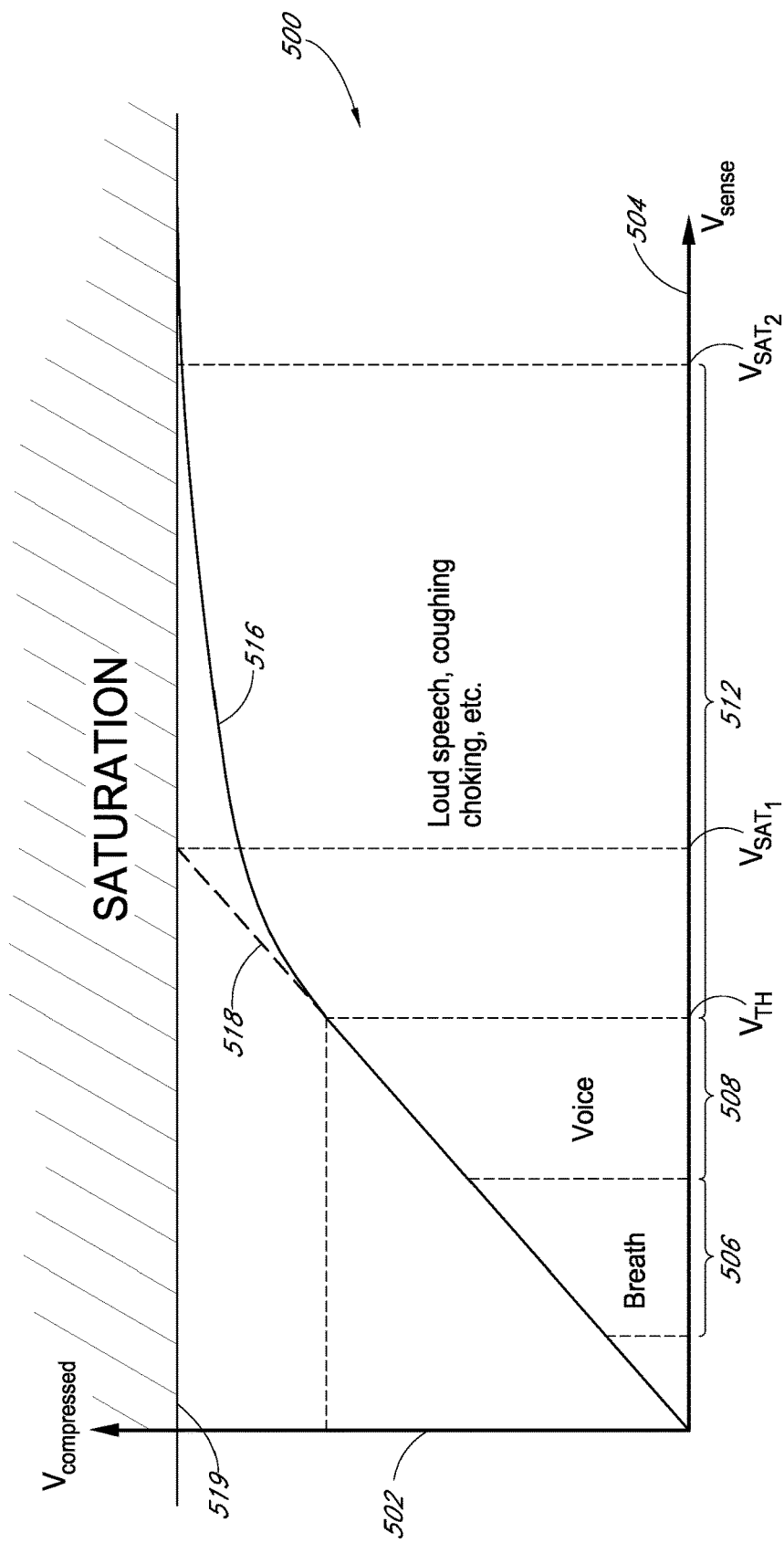
FIG. 5 graphically illustrates a dynamic range compression function implemented by an example sensor according to embodiments of the disclosure.
Figure 10:
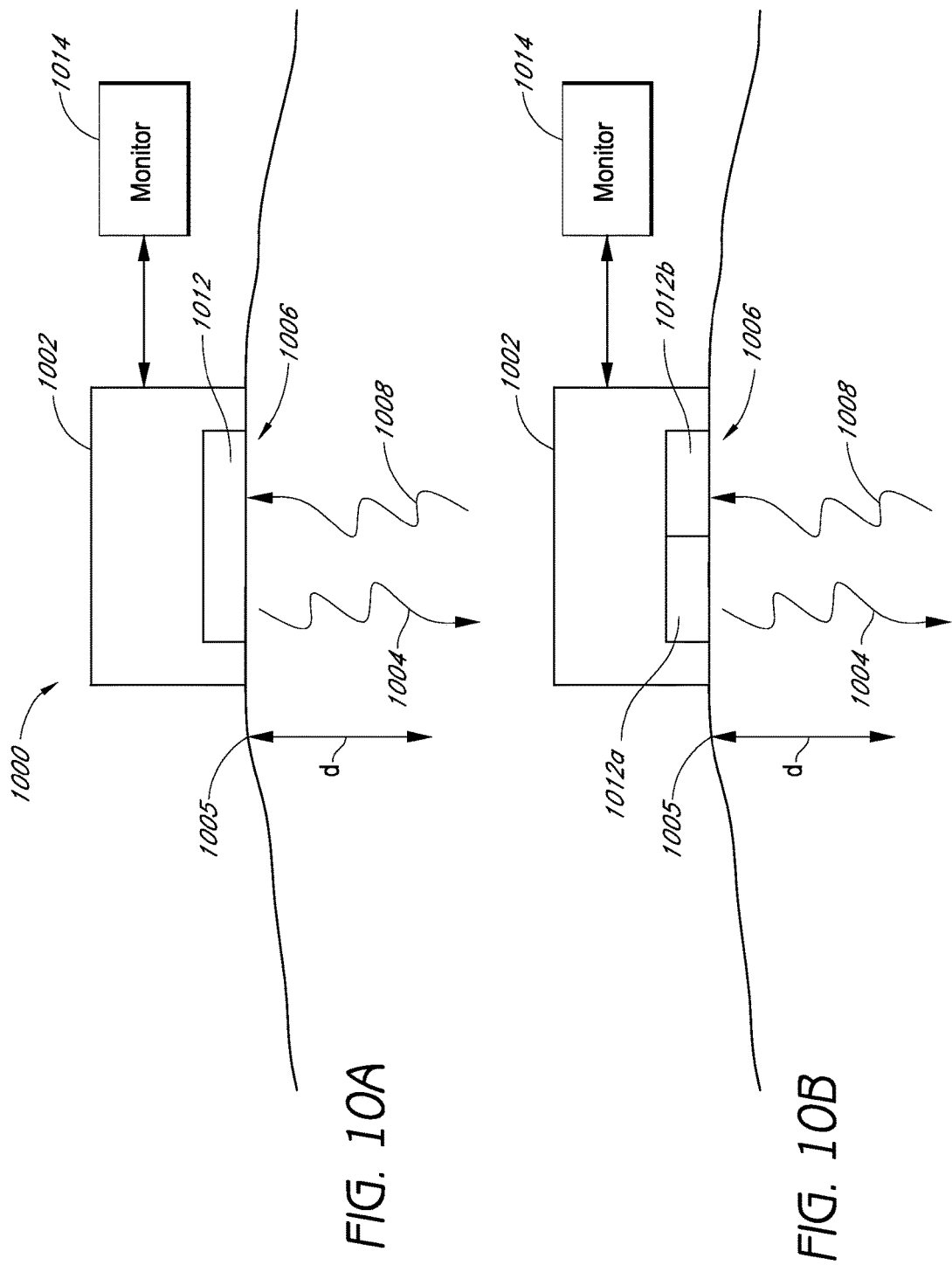
FIG. 10A-B schematically illustrate sensor systems including an active acoustic sensors configured to both transmit acoustic vibrations into a measurement site and receive acoustic vibrations from the measurement site.
Figure 11:
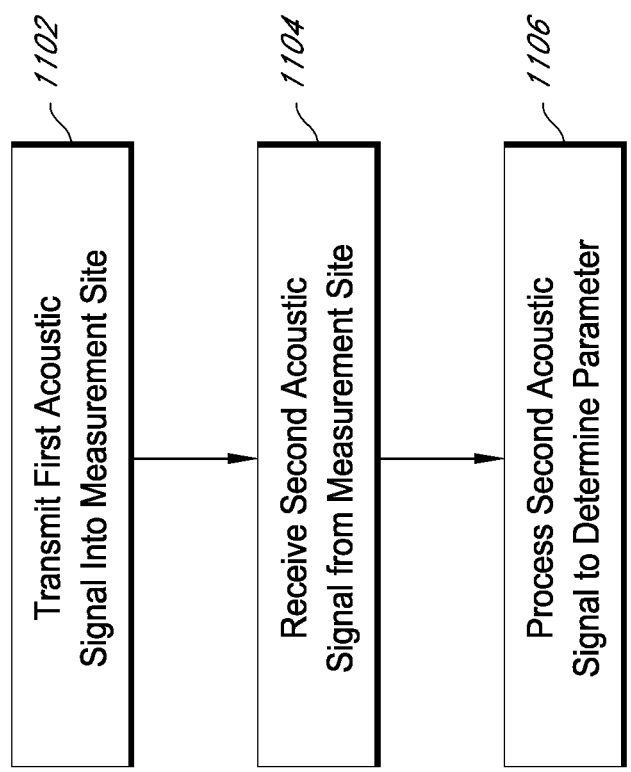
FIG. 11 is a flow chart illustrating a method of using an acoustic sensor in an active configuration.

Referring to the drawings, FIGS. 1A-B, 2 and 12 illustrate example patient monitoring systems, sensors, and cables that can be used to provide acoustic physiological monitoring of a patient, such as respiratory monitoring. FIGS. 4-5 illustrate embodiments of sensors, systems and related techniques capable of improving the operable range of captured physiological sound signals. FIGS. 6A-9 illustrate embodiments of sensors and systems employing multiple sensing elements and/or sensors to provide an improved signal-to-noise ratio according to certain embodiments. Additionally, FIGS. 10A-11 illustrate embodiments of active acoustic sensors. Embodiments of FIGS. 3-11 can be implemented at least in part using the systems and sensors described in FIGS. 1A-1B, 2 and 12.

Figure 1A:
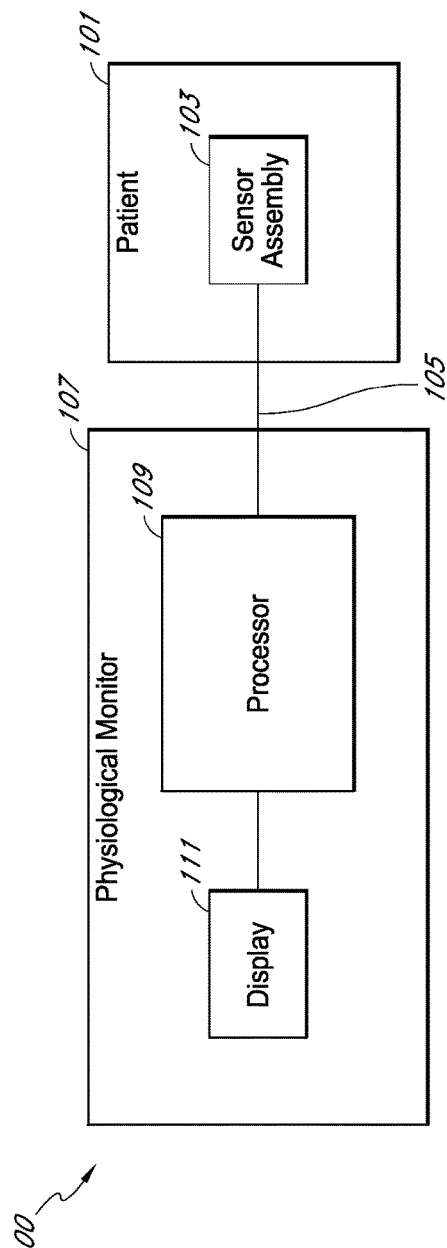
FIGS. 1A-B are block diagrams illustrating physiological monitoring systems in accordance with embodiments of the disclosure.

FIG. 1A illustrates an embodiment of a physiological monitoring system 100. A medical patient 101 is monitored using one or more sensor assemblies 103, each of which transmits a signal over a cable 105 or other communication link or medium to a physiological monitor 107. The physiological monitor 107 includes a processor 109 and, optionally, a display 111. The one or more sensors 103 include sensing elements such as, for example, acoustic piezoelectric devices, electrical ECG leads, or the like. The sensors 103 generate respective signals by measuring a physiological parameter of the patient 101. The signal is then processed by one or more processors 109. The one or more processors 109 then communicate the processed signal to the display 111. In an embodiment, the display 111 is incorporated in the physiological monitor 107. In another embodiment, the display 111 is separate from the physiological monitor 107. In one embodiment, the monitoring system 100 is a portable monitoring system. In another embodiment, the monitoring system 100 is a pod, without a display, that is adapted to provide physiological parameter data to a display.

In some embodiments, the monitor 107 includes a communication module (not shown) that allows the raw sensor signal and/or a processed signal to be communicated to another device. For example, a communications module can wirelessly transmit sensor signal information over a network for remote processing by a remote processing system. In some embodiments, the monitor includes only a communications module.

For clarity, a single block is used to illustrate the one or more sensors 103 shown in FIG. 1A. It should be understood that the sensor 103 block shown is intended to represent one or more sensors. In an embodiment, the one or more sensors 103 include a single sensor of one of the types described below. In another embodiment, the one or more sensors 103 include at least two acoustic sensors. In still another embodiment, the one or more sensors 103 include at least two acoustic sensors and one or more ECG sensors. In each of the foregoing embodiments, additional sensors of different types are also optionally included. Other combinations of numbers and types of sensors are also suitable for use with the physiological monitoring system 100.

In some embodiments of the system shown in FIG. 1A, all of the hardware used to receive and process signals from the sensors is housed within the same housing. In other embodiments, some of the hardware used to receive and process signals is housed within a separate housing. In addition, the physiological monitor 107 of certain embodiments includes hardware, software, or both hardware and software, whether in one housing or multiple housings, used to receive and process the signals transmitted by the sensors 103.

Figure 1B:
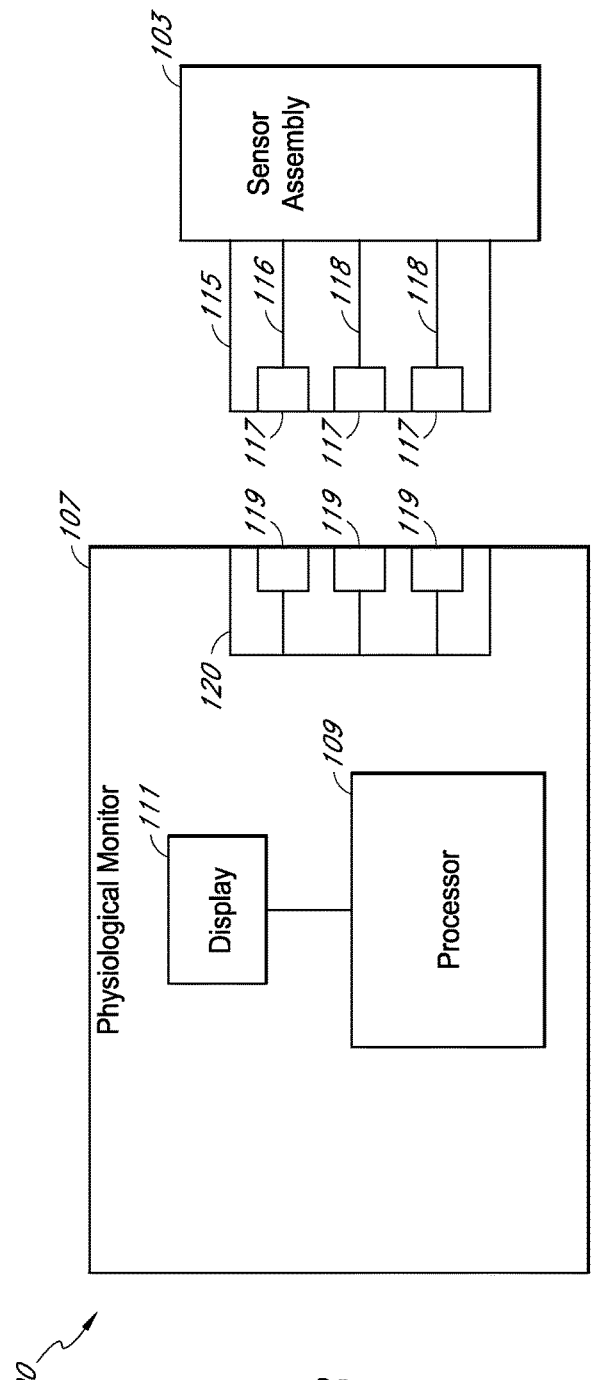

As shown in FIG. 1B, the acoustic sensor assembly 103 can include a cable 115 or lead. The cable 115 typically carries three conductors within an electrical shielding: one conductor 116 to provide power from the physiological monitor 107, one conductor 118 to provide a ground signal from the physiological monitor 107, and one conductor 118 to transmit signals from the sensor 103 to the physiological monitor 107. In some embodiments, the ground signal is an earth ground, but in other embodiments, the ground signal is a patient ground, sometimes referred to as a patient reference, a patient reference signal, a return, or a patient return. In some embodiments, the cable 115 carries two conductors within an electrical shielding layer and the shielding layer acts as the ground conductor. Electrical interfaces 117 in the cable 115 enable the cable to electrically connect to electrical interfaces 119 in a connector 120 of the physiological monitor 107. In another embodiment, the sensor assembly 103 and the physiological monitor 107 communicate wirelessly.

Additional information relating to acoustic sensors compatible with embodiments described herein, including other embodiments of interfaces with the physiological monitor, are included in U.S. patent application Ser. No. 12/044,883, filed Mar. 7, 2008, entitled "Systems and Methods for Determining a Physiological Condition Using an Acoustic Monitor," (hereinafter referred to as "the '883 Application"), U.S. Provisional Application No. 61/141,584, entitled "Acoustic Sensor Assembly", (hereinafter referred to as "the '584 Application"), filed Dec. 30, 2008, U.S. patent application Ser. No. 12/643,939, entitled "ACOUSTIC SENSOR ASSEMBLY," filed on Dec. 21, 2009, (hereinafter referred to as "the '939 Application"), and U.S. patent application Ser. No. 12/904,931, entitled "ACOUSTIC RESPIRATORY MONITORING SENSOR HAVING MULTIPLE SENSING ELEMENTS," filed Oct. 14, 2010, each of which is incorporated in its entirety by reference herein.

Figure 2:
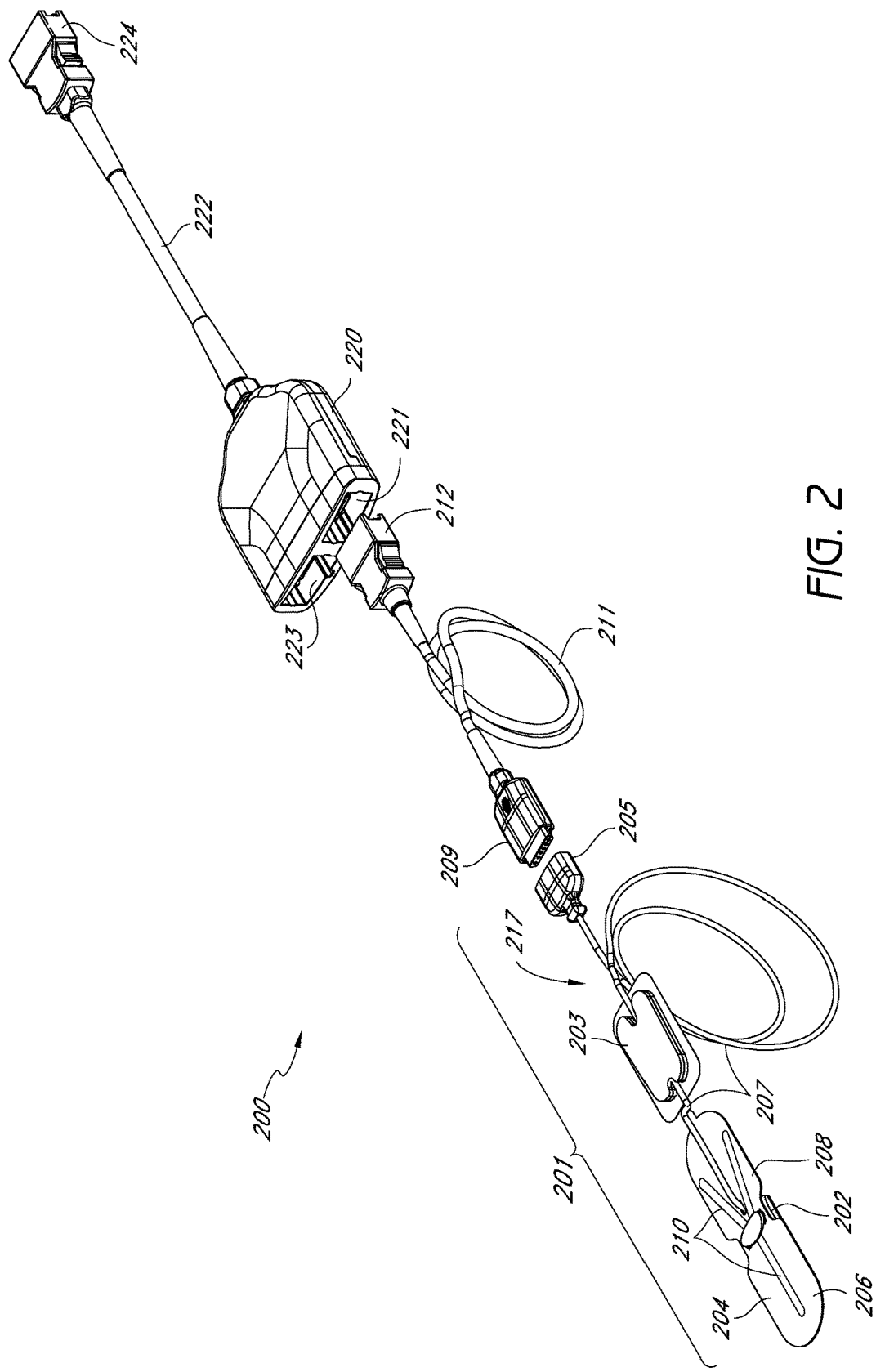
FIG. 2 is a top perspective view illustrating portions of a sensor system in accordance with an embodiment of the disclosure.

FIG. 2 illustrates an embodiment of a sensor system 200 including a sensor 201 suitable for use with any of the physiological monitors shown in FIGS. 1A and 1B. The sensor system 200 includes a sensor 201, a sensor cable 217, a patient anchor 203 attached to the sensor cable 217, and a connector 205 attached to the sensor cable 217. The sensor 201 includes a shell 202 configured to house certain componentry of the sensor 201, and an attachment subassembly 204 positioned the sensor 201 and configured to attach the sensor 201 to the patient.

The sensor 201 can be removably attached to an instrument cable 211 via an instrument cable connector 209. The instrument cable 211 can be attached to a cable hub 220, which includes a port 221 for receiving a connector 212 of the instrument cable 211 and a second port 223 for receiving another cable. In certain embodiments, the second port 223 can receive a cable connected to a pulse oximetry or other sensor. In addition, the cable hub 220 could include additional ports in other embodiments for receiving additional cables. The hub includes a cable 222 which terminates in a connector 224 adapted to connect to a physiological monitor (not shown). In another embodiment, no hub is provided and the acoustic sensor 201 is connected directly to the monitor, via an instrument cable 211 or directly by the sensor cable 217, for example.

The component or group of components between the sensor 201 and the monitor in any particular embodiment may be referred to generally as a coupling apparatus. For example, where one or more of the following components are included, such components or combinations thereof may be referred to as a coupling apparatus: the sensor cable 217, the connector 205, the cable connector 209, the instrument cable 211, the hub 220, the cable 222, and/or the connector 224. It should be noted that one or more of these components may not be included, and that one or more other components may be included between the sensor 201 and the monitor, forming the coupling apparatus.

The acoustic sensor 201 can further include circuitry for detecting and transmitting information related to biological sounds to the physiological monitor. These biological sounds can include heart, breathing, and/or digestive system sounds, in addition to many other physiological phenomena. The acoustic sensor 201 in certain embodiments is a biological sound sensor, such as the sensors described herein. In some embodiments, the biological sound sensor is one of the sensors such as those described in U.S. patent application Ser. No. 12/044,883, filed Mar. 7, 2008, which is incorporated in its entirety by reference herein (the '883 Application). In other embodiments, the acoustic sensor 201 is a biological sound sensor such as those described in U.S. Pat. No. 6,661,161 or U.S. patent application Ser. No. 12/643,939, filed on Dec. 21, 2009 (the '939 Application), both of which are incorporated by reference herein in their entirety. Other embodiments include other suitable acoustic sensors.

In an embodiment, the acoustic sensor 201 includes one or more sensing elements (not shown), such as, for example, a piezoelectric device or other acoustic sensing device. Where a piezoelectric membrane is used, a thin layer of conductive metal can be deposited on each side of the film as electrode coatings, forming electrical poles. The opposing surfaces or poles may be referred to as an anode and cathode, respectively. Each sensing element can generate a voltage potential across the electrical poles that is responsive to vibrations generated by the patient.

The shell 202 according to certain embodiments houses a frame (not shown) configured to support various components of the sensor 201. The one or more sensing elements can be generally wrapped in tension around the frame. For example, the sensing elements can be positioned across an acoustic cavity disposed on the bottom surface of the frame. Thus, the sensing elements according to some embodiments are free to respond to acoustic waves incident upon them, resulting in corresponding induced voltages across the poles of the sensing elements.

Additionally, the shell 202 can include an acoustic coupler not shown), which advantageously improves the coupling between the source of the signal to be measured by the sensor (e.g., the patient's body) and the sensing element. The acoustic coupler of one embodiment includes a bump positioned to apply pressure to the sensing element so as to bias the sensing element in tension. For example, the bump can be positioned against the portion of the sensing element that is stretched across the cavity of the frame.

The attachment sub-assembly 204 in some embodiments includes first and second elongate portions 206, 208. The first and second elongate portions 206, 208 can include patient adhesive (e.g., in some embodiments, tape, glue, a suction device, etc.). The adhesive on the elongate portions 206, 208 can be used to secure the sensor subassembly 202 to a patient's skin. One or more resilient backbone members 210 included in the first and/or second elongate portions 206, 208 can beneficially bias the sensor subassembly 202 in tension against the patient's skin and/or reduce stress on the connection between the patient adhesive and the skin.

While an example sensor system 200 has been provided, embodiments described herein are compatible with a variety of sensors and associated components. For example, compatible acoustic couplers, support frames, attachment subassemblies, sensing elements, and other components are described with respect to FIGS. 19-23 below and in the '939 Application.

Figure 3:
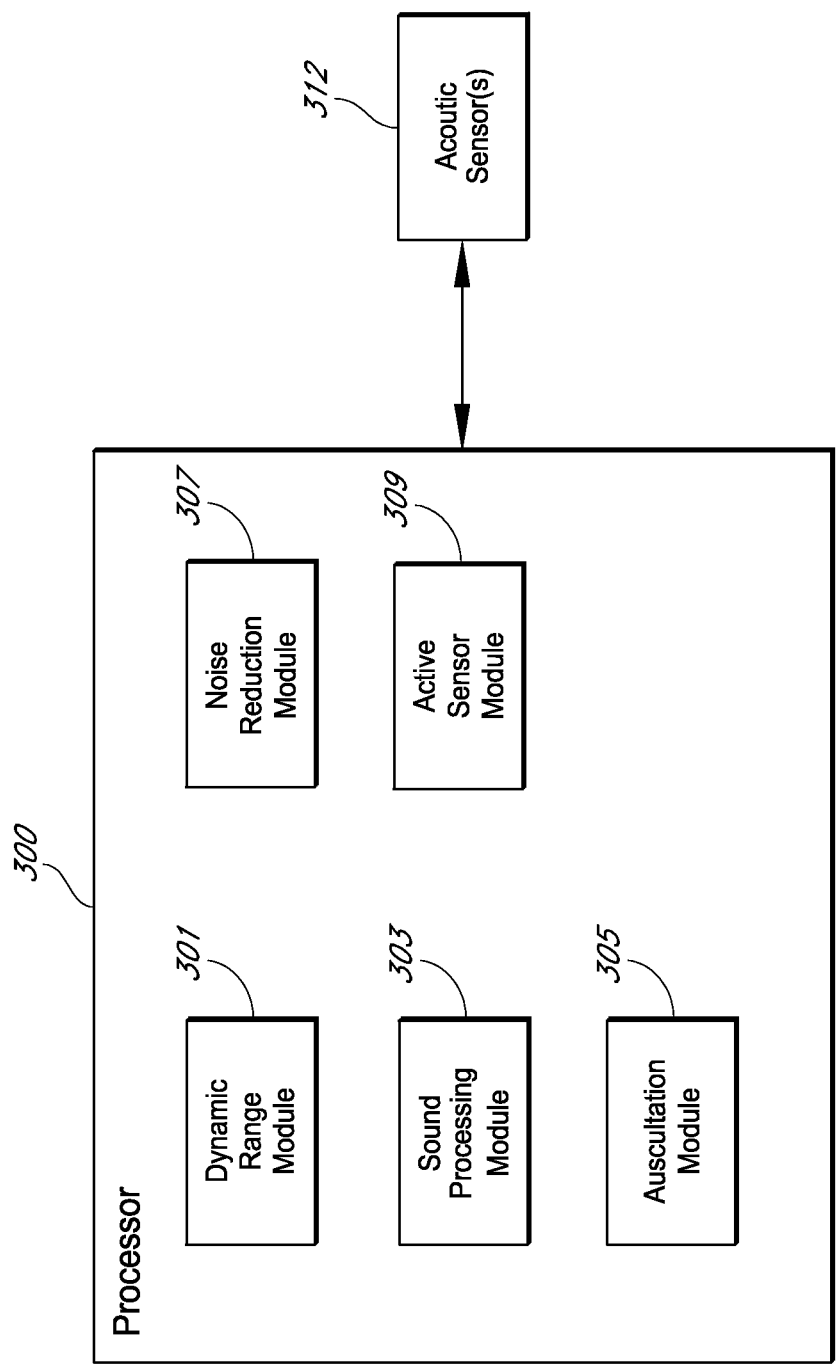
FIG. 3 is a block diagram illustrating a processor of a physiological monitoring system having a plurality of modules implemented thereon according to embodiments of the disclosure.

FIG. 3 is a block diagram illustrating a processor 300 of a physiological monitoring system. The processor 300 communicates with at least one acoustic sensor 312. In certain embodiments, the processor 300 includes one or more of a dynamic range module 301, a sound processing module 303, an auscultation module 305, a noise reduction module 307, and an active sensor module 309.

One or more of the modules are not included in certain embodiments, and any of the individual modules by themselves or any combination of modules can be included. The monitoring system, processor 300, and acoustic sensor(s) 312 may be any of those described herein such as the physiological monitor 100, processor 109, and sensor assembly (or assemblies) 103 of FIGS. 1A-1B, the sensor system 200, sensor 201 and monitor of FIG. 2, the sensor system 1200, sensor 1201 or monitor of FIG. 12, or some other monitoring system, processor and/or sensor assembly, respectively.

As described above, in patient monitoring situations, acoustic sensors can be subject to a very wide spectrum of bodily and other sounds. For example, some bodily sounds, such as breathing and other respiratory sounds may be relatively quiet, corresponding to relatively small acoustical and corresponding electrical signal values. Other physiological sounds, such as loud speech sounds, coughing, choking, gasping, etc., on the other hand, correspond to much larger acoustical and corresponding electrical signal values. The acoustic sensor 312 can include a sensing element (e.g., a piezoelectric film) having a relatively wide input dynamic range, and is therefore capable of detecting relatively low intensity sounds and relatively high intensity sounds without reaching saturation or otherwise distorting. The sensing element can also have a large output dynamic range and thus be capable of producing a signal having a relatively large range of valid, un-distorted, output signal (e.g., voltage or current) values.

One or more subsequent components (e.g., a preamplifier) in the signal processing path, on the other hand, may have a smaller input dynamic range and thus only be capable of processing a smaller range of signal values before reaching saturation, clipping, or otherwise producing a distorted output value. For example, the preamplifier or other relatively low dynamic range component may be configured with a relatively high gain, which may cause saturation for a wider range of input signal values. To reduce losses in captured sound content caused by such saturation, the dynamic range module 301 of certain embodiments generally compresses the signal produced by the sensing element, or otherwise compresses the input signal received by the lower dynamic range component. The compressed signal is then provided to preamplifier or other component in the data path, thereby avoiding saturation for a desired range of sensed signal values, expanding the overall dynamic range of the sensor 300. For example, the ratio of the highest to lowest amplitude sound intensity values that the sensor system 300 can accurately process is increased according to such a technique. In additional embodiments, instead of or in addition to compressing the input to the lower dynamic range component, the output of the lower dynamic range component is compressed directly. Dynamic range improvement is discussed in further detail below with respect to the embodiments of FIGS. 4 and 5.

Such techniques can be useful in a variety of contexts, particularly when relatively loud physiological sounds are expected, such as for voice processing applications or in emergency situations or other situations where it can be beneficial to identify sounds that differ in frequency, amplitude or intensity from the sounds typically sensed by an acoustic sensor. For example, sounds such as coughing, choking, gasping, etc., can be indicative of situations in which intervention from medical personnel may be appropriate, and might not be otherwise detectable if the sensor were to saturate. Such sounds may also be indicative of noise in a respiratory signal. The improved or expanded range of physiological sounds that can be processed using the dynamic range module 301 can be useful in capturing such sounds, particularly where they are relatively loud, for processing.

The sound processing module 303 of certain embodiments accesses a library of sound signatures and compares the received signal with the entries in the library to characterize or identify sounds in the received signal. In another embodiment, the sound processing module 303 generates and/or accesses a library of sound signatures specific to the patient, or specific to a particular type of patient (e.g., male/female, pediatric/adult/geriatric, etc.)

Samples from the patient may be recorded and used to generate the sound signatures. In some embodiments, certain signal characteristics are used to identify particular sounds or classes of sounds. For example, in one embodiment, signal deviations of relatively high amplitude and or sharp slope may be identified by the sound processing module 303. Sounds identified in various embodiments by the sound processing module 303 include, but are not limited to, breathing, speech, choking, swallowing, spasms such as larynx spasms, coughing, gasping, etc.

Once the sound processing module 303 characterizes a particular type of sound, the system 300 can, depending on the identified sound, use the characterization to generate an appropriate response. For example, the system 300 may alert the appropriate medical personnel, modify treatment, etc. In one embodiment, medical personnel may be alerted via an audio alarm, mobile phone call or text message, or other appropriate means.

In one example scenario, the breathing of the patient can become stressed or the patient may begin to choke due to saliva, mucosal, or other build up around an endotracheal tube. Muscle relaxant medication can be given to the patient to alleviate the stressed breathing or choking. In one embodiment, the sound processing module 303 can identify the stressed breathing sounds indicative of such a situation and cause a dosage of muscle relaxant medication to be automatically administered to the patient, or can alert medical personnel to the situation.

Achieving an improved operable range of physiological sounds and/or providing sound processing techniques such as those described above can also be beneficially employed in situations where it is useful to communicate bodily sound information using acoustic sensors. For example, in certain circumstances, it can be useful to communicate bodily sounds (e.g., respiratory sounds, heart sounds, voice sounds, etc.) or bodily sound information derived therefrom.

In certain embodiments, for example, the auscultation module 305 may process the signal received by the acoustic sensor 312 and provide an audio output (e.g., auscultatory output) indicative of internal body sounds of the patient, such as heart sounds, breathing sounds, gastrointestinal sounds, and the like. In some embodiments the auscultation module 305 allows medical personnel to remotely listen (e.g., using a headset or speakers) to bodily sounds for patient diagnosis, communication, etc. For example, medical personnel may listen to the audio output in a different room in the hospital than the patient's room, in another building, etc. The audio output may be transmitted wirelessly (e.g., via Bluetooth, IEEE 802.11, over the Internet, etc.) in some embodiments such that medical personnel may listen to the audio output from generally any location.

The monitoring system 300 may also be capable of recording sounds processed by the auscultation module 305 for later playback or analysis, providing improved diagnostic capability and user flexibility. Additionally, the acoustic sensors described herein according to certain embodiments are generally sanitized prior to each use or may be pre-sanitized, single-use sensors. As such, the audio output functionality described herein may be provide enhanced sanitation as compared to other mechanisms available for listening to bodily sounds (e.g., acoustic stethoscopes) which may become soiled after repeated use. In other embodiments, sensors described herein may be capable of other beneficial functions such as sound recognition, patient communication, and the like. Additionally, the auscultation module 305 can remove the need for a separate auscultatory device, reducing the number of instruments involved in patient monitoring.

In certain embodiments, the auscultatory module 305 allows medical personnel to remotely monitor bodily sounds of the patient. For example, the monitoring system 300 may allow for remote communication with a medical personnel through a listening device (e.g., via cell phone, custom headset, etc.) such that the medical personnel can listen to the bodily sounds of the patient processed by the auscultation module 305.

Additional embodiments of systems employing auscultatory and/or sound processing techniques, or which are capable of providing other related functionality, can be found in U.S. application Ser. No. 12/905,036, entitled PHYSIOLOGICAL ACOUSTIC MONITORING SYSTEM, filed on Oct. 14, 2010, which is hereby incorporated by reference in its entirety herein.

In certain circumstances, acoustical noise such as ambient or environmental sounds can significantly reduce the quality of physiological measurements obtained by the monitoring system 300. Where the monitoring system 300 includes a plurality of sensors 312 or sensing elements, the noise reduction module 307 can be configured to beneficially process the measurement output of a plurality of acoustic sensors 312 attached to a medical patient at a plurality of measurement sites so as to generate an enhanced (e.g., noise reduced) measurement.

The noise reduction module 307 may operate to lower acoustical noise level and/or provide the sensor system 300 with improved noise immunity. The noise reduction module 307 may produce a noise-reduced measurement having an improved signal to noise ratio, for example. In some embodiments, the noise reduction module 307 generates the noise-reduced signal by beneficially employing knowledge of phase relationships (1) between the noise (e.g., ambient noise) components of the acoustic signals received by the sensors and (2) between the components of the acoustic signals received by the sensors indicative of a physiological sounds (e.g., internal bodily sounds indicative of a respiratory sounds).

The noise reduction module 307 may employ a cross-correlation technique in certain embodiments to generate the noise-reduced signal. Example noise reduction systems and methods compatible with the noise reduction module 307 are described herein with respect to FIGS. 6A-9.

Acoustic sensors 312 may be attached to a variety of locations on the patient. The tissue at each location may have specific tissue acoustical characteristics. Knowledge of such characteristics may be useful in monitoring, diagnosis, and/or sensor calibration. Moreover, sensors 312 may be improperly attached or the connection between the sensor and the patient may otherwise be compromised, such as due to yanking or jerking on the sensor 312 or sensor cable. The active sensor module 309 of some embodiments is configured to cause the acoustic sensor 312 to transmit vibrations into the medical patient, receive vibrations coming from the patient in response to the transmitted vibrations, and intelligently process the received signals to determine one or more parameters.

In such embodiments, the active sensor module 309 enables enhanced functionality of the sensor system 300 in addition to measuring physiological parameters. For example, an acoustic signal can be transmitted into the patient and the vibrational response can be measured so as to characterize the tissue to which the sensor is attached, determine the integrity of the mechanical connection between the sensor and measurement site, or for other purposes. Such information can advantageously be used for sensor calibration, alerting medical personnel (e.g., to probe-off conditions), and the like. Example active sensor modules and methods thereof are described herein with respect to FIGS. 10-11, for example.

While each of the dynamic range module 301, sound processing module 303, auscultation module 305, noise reduction module 307 and active sensor module 309 are shown implemented as software modules running on the processor 307, other configurations are possible. For example, one or more of the modules or components thereof may be implemented in hardware, such as in custom circuitry, programmable logic (e.g., in a programmable logic array), or in an application-specific integrated circuit(s). In some embodiments, the modules or components there of are implemented across multiple processors. In one embodiment, the modules are remotely implemented on one or more processors in communication with the physiological monitor 300 over a network.

Dynamic Range Improvement

FIG. 4 is a schematic diagram of one embodiment of a sensor system 400 including a sensor 401 coupled to a patient 403, and a physiological monitor 409 in communication with the sensor 401. The system 400 generally includes componentry enabling the system 400 to process a wider dynamic range of sound intensity values.

The illustrated sensor 401 includes a sensing element 408, a compression module 402, and front-end componentry 404. The monitor 409 includes one or more processors 416, and can include a decompression module 418. The monitor is generally configured to process the signal 412 received from the sensor 401, and in some embodiments is configured determine, display, or otherwise output, one more physiological parameters (e.g., respiratory rate, heart rate, etc.) of the patient as described herein. The monitor 409 and sensor 401 can generally be any of the sensors described herein, for example, such as any of the sensors or monitors described above with respect to FIGS. 1-3 and 6-12 or incorporated by reference herein. The monitor 409 according to various embodiments can include one or more acoustic front-ends, analog to digital converters, a digital signal processor (DSP), and the like. The DSP can comprise a wide variety of data and/or signal processors capable of executing programs for determining physiological parameters from input data.

As is described herein, the compression module 402 and/or decompression module 418 generally work together to improve the dynamic range of the sensor 401 so as to widen the range of physiological sound content that can be accurately processed by the sensor 401. Thus, the compression module 402 and/or decompression module 418 can be referred to as a dynamic range module and can be included in the dynamic range module 301 of FIG. 3, for example.

The front-end componentry 404 is shown and described with respect to the illustrative embodiment and other embodiments herein as a separate component from the compression module 402. However, in other embodiments, the compression module 402 and the front-end componentry 404 or portions thereof can be arranged differently with respect to one another. For example, the compression module 402 and front end componentry 404 can be arranged in a feed-back and/or feed-forward arrangement, examples of which are shown in FIGS. 4B-4D, discussed below. Moreover, the compression module and the front-end 404 componentry or a subset thereof may form the same circuit in some embodiments. For example, in one embodiment, the front-end componentry 404 includes a preamplifier circuit configured both to compress the sensed signal 407 according to compression techniques described herein and also pre-amplify the signal 407.

An illustrative example embodiment will now be described. The example embodiment, the sensing element 408 is a piezoelectric film having a relatively high input dynamic ranges, and is wrapped around a frame in tension as described above with respect to the sensor 201 of FIG. 2. The sensing element 408 detects an acoustic signal 405 (e.g., physiological sounds) from the patient 403 and produces a corresponding electrical signal 407 (e.g., a voltage signal). The sensing element 408 has a relatively large output dynamic range, and the signal 407 thus has a relatively large range of possible un-distorted values. For example, the output dynamic range may be relatively larger than a subsequent component in the sensor data path, such as a preamplifier, as described below.

In certain embodiments, the preamplifier and/or other front-end componentry 404 generally decouple the power supply (not shown) and performs preliminary signal processing. The front-end componentry 404 can include clamping diodes to provide electrostatic discharge (ESD) protection and a mid-level voltage DC offset for the piezoelectric signal to ride on, to be superimposed on or to be added to. The front-end componentry 404 may include a preamplifier circuit residing in one embodiment to provide gain to the sensed signal. The front-end componentry 404 may also have a high pass filter to eliminate unwanted low frequencies such as below about 100 Hz for breath sound applications, and an op amp to provide gain to the piezoelectric signal. The front-end componentry 404 may have a low pass filter at the output of the preamplifier to filter out unwanted high frequencies. In an embodiment, a high pass filter is provided on the output in addition to or instead of the low pass filter. The front-end componentry 404 may also provide impedance compensation to the signal, such as a series/parallel combination used to control the signal level strength and frequency of interest that is input to the preamplifier. In one embodiment, the impedance compensation is used to minimize variation in the sensed signal. The impedance compensation can be constructed of any combination of resistive, capacitive and inductive elements, such as RC or RLC circuits. In some embodiments, the preamplifier can be configured to amplify a relatively low level detected signal to a line-level signal 412 for transmitting to the monitor 409 over a cable (not shown). As described, the preamplifier and/or other front-end componentry can additionally or alternatively be configured to balance reduce signal impedance before transmitting the signal over the cable, reduce system noise by introducing signal gain before one or more noisy stages in the data path, or a combination thereof. The preamplifier in the example embodiment is capable of processing a relatively smaller input dynamic range than the output dynamic range of the sensing element 408. Thus, the differential range of input voltage signals the preamplifier can process without producing a distorted output is smaller than the differential range of output signals produced by the sensing element 408. Thus, without dynamic range compression, the preamplifier would saturate for certain values of the signal 407 falling in the output dynamic range of the piezoelectric film 408.

To reduce undesirable losses in sound content due to such saturation or other distortion, the compression module 402 according to the example produces a signal 410 corresponding to a compressed version of the sensed signal 407. The compression scheme may be selected based on the input dynamic range of the preamplifier, for example. A plot 500 showing values of a compressed signal generated by a compression module 402 is shown in FIG. 5. Referring now to FIGS. 4 and 5, the plot 500 shows compressed signal 410 values (axis 502) generated by the compression module 402 for given signal values 407 (axis 504) produced by the sensing element 408. Signal values above the line 519 will cause the preamplifier to saturate or otherwise produce a distorted output.

The linear portion of the compressed signal 410 curve along the dotted line 518 corresponds to values of the sensed signal 407 falling below a threshold sensed signal 407 voltage ($V_{TH}$). According to the example embodiment, the compression module 402 does not compress the sensed signal 407 for values below $V_{TH}$ and the signal 410 thus corresponds to an unmodified version of the signal 407 for such values. Passing an unmodified version of the input signal for at least some sensed signal 407 values can advantageously preserve resolution in the sound content corresponding to such values, as is described in more detail below.

As indicated by the dotted line 518, if the compressed signal 410 is presented to the preamplifier as an unmodified version of the sensed signal 407 for signal 407 values above $V_{SAT1}$, the preamplifier will saturate. Thus, the compression module 402 produces a compressed version of the sensed signal 407 for signal 407 values above $V_{TH}$, as illustrated by the curve 516. The compression module 402 of the example embodiment performs a logarithmic function on the sensed signal 407. For example, the compression module includes a logarithmic amplifier configured to produce a compressed or otherwise reduced or attenuated signal 410 according to the curve 516. A wide variety of other compression schemes can be employed in other embodiments, as will be described below.

As shown, compressed signal values 410 along the curve 516 generally gradually approach the preamplifier saturation region. Thus, the compressed signal 410 reaches saturation for an input voltage value $V_{SAT2}$ which is significantly higher than $V_{SAT1}$, without compression. As such, the preamplifier generally will operate without saturating or otherwise distorting for a wider range of sensed signal 407 values, improving the overall dynamic range of the sensor 400.

As shown, certain characteristic bodily sounds may generally correspond to various regions of the plot 500. For example, in one embodiment, sensed signal 407 values falling in the regions 506, 508 generally correspond to breathing and typical voice sounds, while sensed signal 407 values falling in the region 512 correspond to relatively louder sounds such as loud speech, snoring coughing, choking, and/or other higher volume physiological sounds. As shown, in the example embodiment, use of the compression module 402 advantageously avoids preamplifier saturation for a wider range of sensed signals 407 corresponding to relatively louder sounds in the region 512.

Due to the compression, the signal received by the monitor 409 can include distortive effects, and the decompression module 418 is generally configured to remove or reduce such distortive effects. In the example embodiment, the decompression module 418 includes a software module executing on the processor 416 of the monitor 409, and is configured to perform the mathematical inverse of the function performed by the compression module 402. Other de-compression techniques are possible, and some are described below.

While described with respect to the above example for clarity, the implementation of the various components of the system can vary. For example, FIGS. 4B-4C show example alternative arrangements in which a compression module 402 is arranged in feed-back and feed-forward relationships with respect to the front-end componentry, respectively. In the feed-back configuration of FIG. 4B, the compression module 402 generally compresses the input to the front-end componentry 404 (e.g., the sensing element output signal) in response to front-end componentry 404 output. In a feed-forward configuration, the compression module 402 compresses the output of the front-end componentry rather than compressing the input. In some embodiments, a combination of feed-back and feed-forward configurations are used.

FIG. 4D illustrates a diagram of an example circuit 450 configured to perform dynamic range compression according to one embodiment. The circuit 450 includes an operational amplifier U1 arranged in a non-inverting, differential configuration with a pair of resistors R1, R2. For the purposes of illustration, the circuit 450 is shown as including an AC voltage source V2 biased by a DC offset voltage V1. In some embodiments, the AC voltage source 420 is representative of the electrical output of a sensing element (not shown). Thus, the signal 452 is representative of the sensing element output signal or a signal derived therefrom.

The operational amplifier U1 and resistors R1, R2 generally form a preamplifier circuit configured to pre-amplify the sensing element signal 452. For example, in one embodiment, the preamplifier has a gain of two and produces a pre-amplified signal 456 which is generally double the input signal, although a multitude of other preamplifier configurations are possible. However, as described herein, the preamplifier may have a relatively low dynamic range and may saturate for certain desired values of the input signal 452.

To improve the dynamic range of the preamplifier, a compression module including a pair of diodes D1, D2 connected between the output of the operational amplifier U1 (which is also the preamplifier output) and the non-inverting input of the operational amplifier U1. As shown, the diodes D1, D2 are connected in parallel and in opposite polarity with respect to one another. Generally speaking, the compression module including the two diodes D1, D2 compresses the preamplifier output when the output signal 456 falls within certain predetermined ranges. For example, in one embodiment, when the output signal 456 is greater than a first threshold value, the compression module compresses the output signal 456, reducing the effective gain of the preamplifier from two to one. Conversely, when the output signal 456 is less than a second threshold value, the compression module reduces the gain of the output signal 456 from two to one. A variety of threshold values are possible. For example, where the output signal 456 is an AC signal that is positively biased by a DC offset, the first and second threshold values may be selected generally symmetrically about the DC offset such that compression occurs symmetrically with respect to the positive and negative signal peaks. In other embodiments, where the output signal 456 is an AC signal that alternates between positive an negative values, the threshold values may comprise positive and negative values of equal magnitude, respectively. In other embodiments, asymmetric threshold values can be used, or only one peak of the AC signal is compressed.

Referring again to FIG. 4A, depending on the desired compression scheme, the compression module 402 can be configured to perform a wide variety of functions on the sensed signal 407. For example, the compression module 402 can implement one or more of a variety of linear functions (e.g., scalar functions), logarithmic functions, or other types of linear, non-linear functions, or combinations thereof. In some embodiments, the function implemented by the compression module 402 corresponds to a polynomial function having a set of corresponding coefficients and/or an offset. In one embodiment, the function is a third order polynomial, although other order polynomials can be used.

Generally, the amount or quality of compression used can be selected based on a trade-off between the compression achieved and the resolution of the sensed signal that is preserved. For example, in the example shown in FIG. 5, signal values corresponding to breathing and voice sounds are uncompressed, thereby preserving resolution with respect to those sounds. On the other hand, signal values corresponding to louder sounds are compressed, resulting in a loss of resolution, but an increase in the range of such sounds that can be captured. Because breathing and voice sounds are relatively low intensity, it can be beneficial to maintain resolution to more readily distinguish fluctuations in sound levels (e.g., for physiological monitoring or remote listening purposes). The compression scheme of FIG. 5 advantageously allows for preserves resolution for quieter sounds while still allowing louder sounds to be processed.

In other embodiments, the compression module 402 compresses the signal 407 for all sensed signal 407 values, thereby further increasing the overall dynamic range of the sensor. In such cases, the compression module 402 may implement only one function for all sensed signal 407 values, or may implement a first function for signal values below a threshold voltage, and a second function for values at or above the threshold. In other embodiments, three, four or more functions and corresponding thresholds can be used. In one embodiment, the compression is generally piece-wise linear, and the compression module 402 compresses the signal 407 according to a first slope when the signal exceeds a first threshold and compresses the signal 407 according to a second slope when the signal exceeds a second threshold value, and so forth. The term "multi-stage compression" may refer to embodiments where more than one function or curve is applied for different input signal value ranges.

Depending on the embodiment and corresponding compression scheme, the compression module 402 can include a variety of circuitry, including one or more amplifiers (e.g., operational amplifiers), comparators, multiplexors, combinations of the same and the like. The amplifier circuits can include linear (e.g., scalar), non-linear, logarithmic amplifiers, etc.

In various embodiments, the sensing element 408 can include generally any acoustic transducer or other type of acoustic sensing device, such as any of those described herein.

The front-end componentry 404 may include one or more additional components instead of, or in addition to a pre-amplifier. For example, the front-end componentry 404 can generally include any circuitry or other componentry configured to condition the signal for later processing. Such circuitry can include analog circuitry such as one or more operational amplifiers, filters (e.g., high, low or bandpass filter), analog to digital converters, diodes, combinations of the same or the like. Moreover, where the front-end componentry 404 includes multiple components, any of the components can receive the compressed signal 410.

Moreover, the arrangement of the components shown residing on the sensor 400 may physically reside at some other location. For example, one or more of the components of the compression module 402 and/or front end componentry 404 can reside at some intermediate location (e.g., a cable, connector or hub) between the sensor 400 and the monitor 409, or can reside on the monitor 409 itself. In one embodiment, the compression module 402 is coupled to some other component in the sensor data path not residing in the front end 404.

Also, while not shown for the purposes of clarity, in certain configurations a variety of other circuitry or other componentry may be interposed between, or be otherwise connected to the various components. Moreover, the relative order of the compression module 402 and other components can be swapped or otherwise rearranged. For example, in one embodiment, the front-end componentry 404 includes multiple stages, and the compression module 402 resides between two of the stages. In another embodiment, multiple compression modules 402 reside between appropriate components in the data path.

While the signal 407 is referred to herein as the sensed signal 407 and is shown as being received by the compression module 402 directly from the sensing element 408 for the purposes of illustration, the signal 407 in certain embodiments is modified by one or more components disposed between the sensing element 408 and the compression module 402. In a similar fashion, the sensing element signals of FIGS. 4B-4C and the signal 452 of FIG. 4D may be modified by one or more other components before reaching the respective front-end componentry and/or compression module.

As described, the decompression module 418 receives the conditioned signal 412 and is configured to generally remove distorting effects introduced by the compression or modification process. In certain embodiments, the decompression module 418 has a very high numerical dynamic range and can thus numerically represent, without saturation, the uncompressed or otherwise unaltered signal 407 produced by the sensing element 408. While described in the above example as performing the mathematical inverse of the compression function, in some cases, the decompression module 418 does not perform the exact inverse of the function performed by the compression module 402. Instead, the decompression module 418 can perform some function approximating or otherwise based on or derived from the inverse, or otherwise generally reversing the compression.

For example, in some embodiments, coefficients of a polynomial representation of the compression function are stored in one or more memory devices. The decompression module 418 retrieves the coefficients and uses them to reconstruct the generally unaltered, pre-compressed sensed signal 907. A third order polynomial is used in one embodiment. In such an embodiment, the decompression module 418 retrieves three coefficients and/or an offset value stored in an EPROM or other memory device and uses the values to decompress the signal.

As described; according to certain embodiments, the compressed signal 410 is generally a compressed version of the sensed signal 407, or portions thereof. Similarly, where the output of the front-end componentry 404 is directly modified, it is generally modified to generate a compressed version of the front-end output according to many of the embodiments described herein. Thus, the dynamic range modification is described generally throughout the disclosure as compression, dynamic range compression, and the like. However, in some cases, other forms of dynamic range improvement compatible with embodiments described herein do not involve compressing the sensed signal 407, or involve compressing for some signal values and not compressing for other signal values. In some embodiments, for example, a linear function (e.g., implementing a scalar multiplying factor) having a slope greater than one, or some other non-compressive function is implemented by the compression modules described herein. Moreover, while dynamic range improvement and compression is described in terms of signal magnitudes, in certain embodiments, other types of dynamic range improvement can be achieved. For example, the ratio of the highest and lowest acoustic frequencies that can be processed by the sensor system 400 can be improved according to certain compatible embodiments.

In some alternative embodiments, the sensor system 400 allows for the configuration or selection of the desired compression function. For example, depending on the desired application, a user may select from a plurality of modes implementing a variety of different functions. As one illustrative example scenario, a user may select a first mode implementing a first function suitable for relatively quiet conditions when the monitoring environment is relatively quiet. Conversely, the user may select a second mode implementing a second function suitable for relatively loud conditions when the monitoring environment is relatively loud. Modes and associated functions can be tailored for any number of situations, e.g., based on the type of physiological sound being monitored, whether it is desirable to capture patient speech sounds, etc.

In other embodiments, the compression function or functions employed by the compression module 402 are automatically selected by the system 400 based on certain predetermined criteria. For example, while other criteria can be used, in one embodiment, the system 400 automatically changes the compression function when it detects a saturation condition or threshold number of saturation conditions at a relevant location or locations within the data path 401. The automatic selection can be based on an averaging or other operation performed on captured sound intensity values for a given period of time, on detection of a particular type or quality of detected sounds, such as the detection of speech sounds, or the like.

Additional Applications

According to some embodiments, acoustic sensors incorporating certain acoustical design advantages described herein can be used in an array of beneficial applications. Such applications described herein include enhanced monitoring of physiological parameters (e.g., respiratory parameters), auscultation (e.g., as described with respect to the auscultation module 305 of FIG. 3), sound characterization and identification (e.g., as described above with respect to FIG. 3), active sensor applications, etc.

Additionally, sensor systems of some embodiments are configured to be used as a microphone so as to allow for patient communication. For example, the sensor system may be adapted to transmit patient vocal communications to devices incorporating speakers, such as cell phones, walkie-talkies or other radio devices, remote patient monitors, etc. In one embodiment, appropriate medical personnel are equipped with such devices so that the patient can remotely communicate with them. For example, the patient monitor applies an appropriate filtering function to the signal received by the acoustic sensor in order to generate the audio output. In one embodiment, the acoustic sensor system includes a button on the sensor that allows the patient to activate the remote vocal communication functionality. In other configurations, a button may be located elsewhere to activate vocal communication, such as on the patient's bed, on the physiological monitor, etc. The button may alert a nurse or other medical personnel that the patient wants to communicate using the sensor, for example.

Such patient communication capability can allow for medical personnel to respond to emergency situations quickly and efficiently as compared to existing communication mechanisms such as button alarms which may not allow for voice communication and can be difficult for patient's to locate and operate, particularly in emergency situations. In some embodiments, the sensor can also be used as a speaker such that the medical personnel or others can remotely speak to the patient, thereby allowing for two-way communication.

The acoustic sensors described herein according to certain embodiments are generally sanitized prior to each use or may be pre-sanitized, single-use sensors. As such, the audio output functionality described herein may be provide enhanced sanitation as compared to other mechanisms available for listening to bodily sounds (e.g., acoustic or electronic stethoscopes) which may become soiled after repeated use. In other embodiments, sensors described herein may be capable of other beneficial functions such as sound recognition, patient communication, and the like.

Noise Reduction Using Multiple Sensors

FIG. 6A is a top view of an embodiment in which a plurality of acoustic sensors 602 are attached to various locations spaced about a patient's neck 608. The illustrated configuration can be used to generate a noise-reduced acoustical signal. Signals from the sensors 602 are communicated to a physiological monitor 601, which generates the noise reduced signal. In the example embodiment, first, second, and third acoustic sensors 602 comprising first, second and third sensing elements 603, are used. Other numbers of sensors (e.g., 2, 4, 5, or more) can be used in other configurations.

In general, the acoustic vibrations detected by the sensing elements 603 (e.g., a piezoelectric element) of the sensors 601 include bodily acoustic sounds 610 indicative of physiological parameters (e.g., breathing sounds indicative of respiratory rate, heart sounds, etc.). Additionally, the sensing elements 603 may detect acoustic vibrations 612 from environmental noise (sometimes referred to as ambient noise) emanating from one or more noise sources 614. As a result, the each of the individual sensing elements 603 will produce an electrical signal indicative of detected acoustic vibrations. Each electrical signal will therefore include a physiological sound component representative of the physiological parameter and a noise sound component representative of environmental and/or other noise.

In some embodiments, the acoustic noise sounds 612 include acoustic signals that do not emanate from the patient, but are detected by the sensors 602. For example, the noise sounds 612 may include noise from an external noise source 614, such as electronics (e.g., computers, medical equipment, motors, pumps, fans, alarms, or other electronics, etc.), noise from other people such as visiting family members and medical personnel in the vicinity of the patient, vehicle noise (e.g., in an ambulance), etc. In some embodiments, the noise sounds 612 include acoustic sounds coming from the patient that are not indicative of measured physiological parameters. Such sounds may include patient speech, coughing, etc.

The signal-to-noise ratio of the sensor signals is generally reduced due to the presence of the noise sounds 612. In some circumstances, a reduced signal-to-noise ratio can make it difficult to distinguish the physiological sound components of the signal from the noise components to provide accurate measurements. In certain embodiments, signals from the plurality of sensors 602 indicative of the noise sounds 612 and the bodily sounds 610 are advantageously processed (e.g., by the processor of the physiological monitor 601) so as to generate a noise reduced signal having a higher, improved signal to noise ratio than that of the individual sensor signals. Such techniques may operate to lower the ambient acoustical noise level and/or provide the sensor system with improved noise immunity.

In general, noise sounds 612 may include signals travelling at slower speeds and/or lower frequencies than the bodily acoustic sounds 610. For example, the noise sound 612 may generally travel through the air at the speed of sound, about 343 meters per second in some circumstances. As such, although the sensors 602 are spaced from each other, the noise sounds 612 generally arrive at the sensors 602 in phase or substantially in phase. For example, noise sounds 612 arriving at one of the sensors 602 arrives at substantially the same time, or relatively close to the same time as the noise sounds 612 arrive at the other sensors 602, and/or arrive in the same or substantially the same phase relationship.

The bodily sounds 610, on the other hand, generally travel at increased speeds and/or at higher frequencies than the noise sounds 612. In one embodiment, the bodily sounds 610 travel at about 1500 m/s through the patient's body. Because the bodily sounds 610 travel at an increased speed, the physical separation of the sensors 602 causes the bodily sounds 610 to arrive at the sensors 601 out of phase or substantially out of phase with one another. For example, the bodily sounds 610 may arrive at one of the sensors 602 at a significantly different time than the noise arriving at the other two sensors 602. In one embodiment, the bodily sounds 610 arrive at the sensors 602 significantly more out of phase, with significantly more time of arrival difference and/or phase difference between the sensors 602 than the noise sounds 612.

In certain embodiments, the sensor system advantageously utilizes the knowledge of the phase relationship between the noise sounds 612 arriving at the plurality of sensors 602 as compared to the phase relationship between the bodily sounds 610 arriving at the plurality of sensors 602 so as to generate a reduced noise signal. For example, the monitor of the sensor system may receive signals including both the noise sound 612 components and the bodily sound 610 components detected by the sensors 602. The system can operate to generate a noise reduced signal having a higher, improved signal to noise ratio than that of the signals from the individual sensor signals. For example, the noise reduction module may employ a cross-correlation technique in generating the noise reduced signal. This general noise reduction process may sometimes be referred to as a common mode rejection technique because components of each of the acoustic signals received by the sensors that were in-phase, or "common" (the noise sounds 612) are generally reduced or "rejected."

In one embodiment, the sensor system is configured to shift the signals from one or more of the sensors 602 with respect to the other sensor 602 signals, shifting the bodily sound components 610 of the sensor 602 signals in phase. The noise sound 612 components, on the other hand, are shifted out of phase with respect to one another. The shifted and un-shifted signals can be combined (e.g., summed together) to form a noise reduced signal.

Because the bodily sound components 610 are shifted to be in phase, they generally constructively interfere or otherwise combine in an additive manner. Moreover, the sensor 602 signals may be combined in an additive manner because the bodily sound components 610 may be coherent or substantially coherent relationship with respect to one another.

On the other hand, because the noise components 612 are shifted out of phase, they do not constructively interfere. For example, the noise components may destructively interfere or otherwise be combined in a non-additive manner. Moreover, the sensor 602 signals may combine in a non-additive manner because the noise sound components 612 may be in a non-coherent or substantially non-coherent relationship with respect to one another. As a result, the bodily sound components 610 of the noise reduced signal are increased relative to the noise signal components 612, thereby improving the signal to noise ratio of the noise reduced as signal as compared to the sensor 602 signals.

Figure 6B:
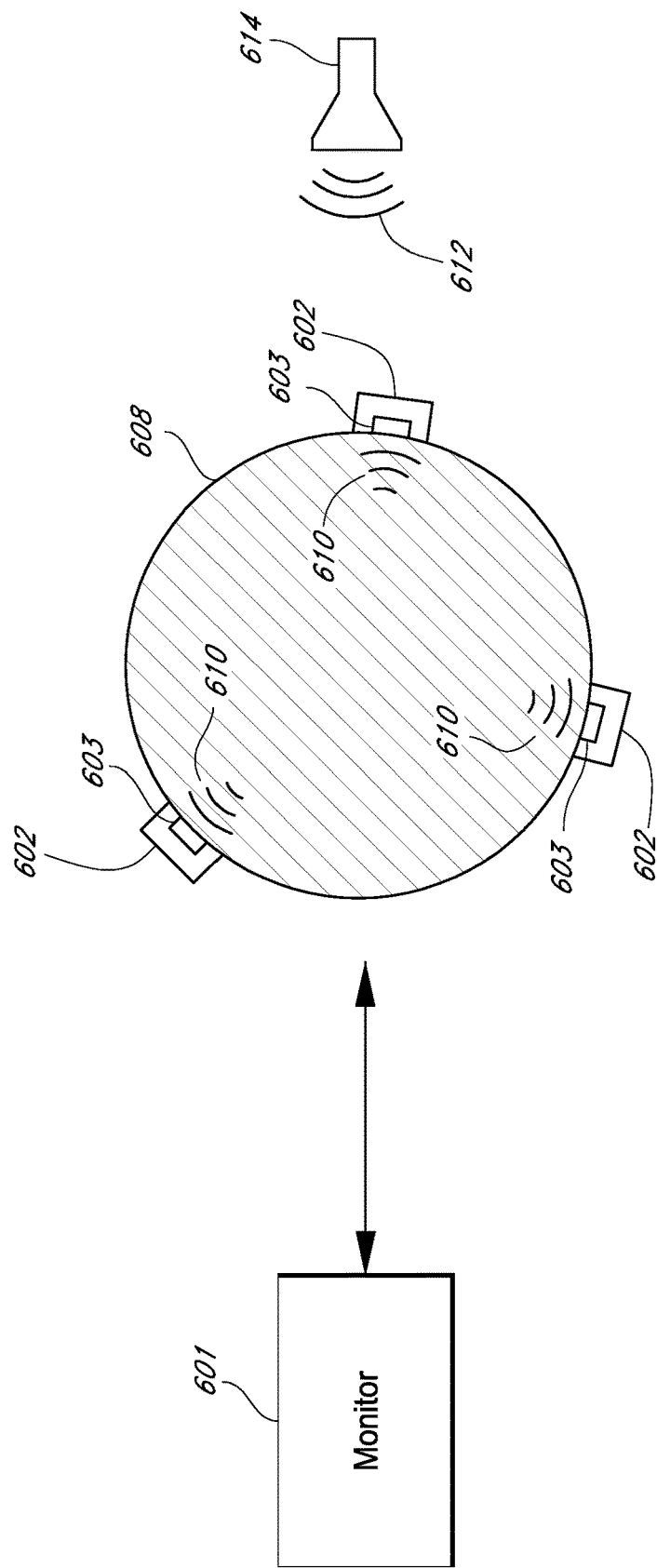

FIG. 6B is a top view of an embodiment in which a plurality of sensors 602 are spaced relatively far apart from one another. Such spatial separation can introduce more drastic differences in the phase relationship and/or signal intensity between the bodily sound components 610 of the signals.

Referring again to FIG. 6A, the plurality of sensors 602 positioned relatively closer together on the patient's neck 608 than in the embodiment of FIG. 6B. In one embodiment, the sensors 602 are coupled to a single attachment element and attached to the patient generally as a group. In contrast to the arrangement of FIG. 6B, the arrangement of FIG. 6A does not involve relatively long cables between the sensors 602. As such, signal noise and/or bulk which may be introduced by the use of such cables is avoided. In one embodiment, the sensors 602 comprise a plurality of sensing elements within a single sensor package (e.g., attached to a single sensor frame or support). Generally, any configuration having some physical separation of the sensing elements 603 may be compatible with certain embodiments described herein.

In certain embodiments, one or more of the plurality of sensors 602 includes an electrical shielding barrier such as those described above. The multi-sensor noise reduction technique can operate in conjunction with electrical shielding barriers to improve overall noise reduction. For example, the techniques may combine synergistically to increase the signal-to-noise ratio, lower the noise floor, and/or improve the noise immunity of the system. In certain embodiments, the shielding barrier can reduce a first type of noise, while the noise reduction module 607 reduces a second type of noise. In one embodiment, the shielding barriers primarily reduce electrical interference (e.g., from external static electrical fields and electromagnetic fields) incident on the sensors while the noise reduction module 607 reduces acoustical noise.

Figure 7:
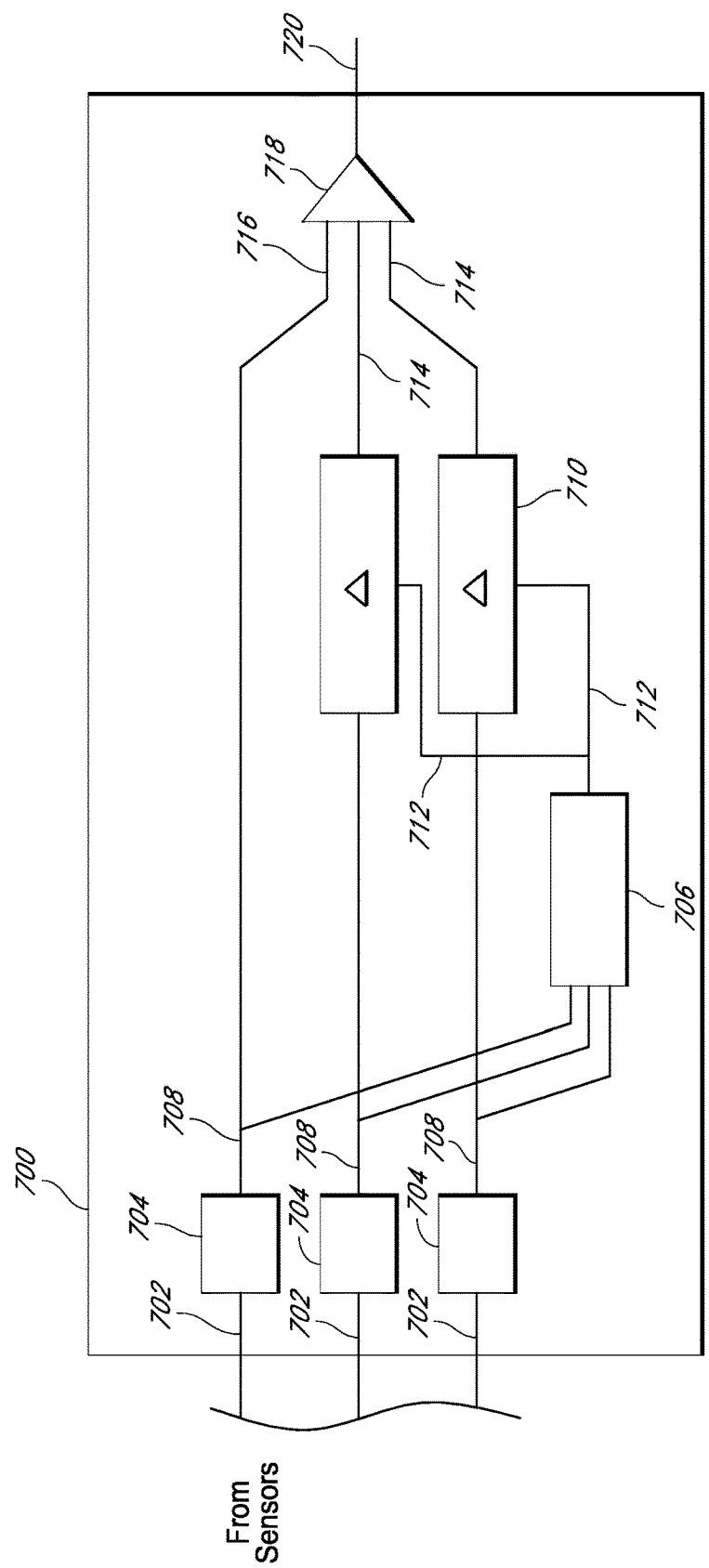
FIG. 7 is a block diagram illustrating a noise reduction module configured to process signals from multiple sensors according to embodiments of the disclosure.

FIG. 7 is a block diagram illustrating a noise reduction module 700 employing a cross-correlation technique to process a plurality of signals 702 from a plurality of sensors according to embodiments of the disclosure. The noise reduction module 700 outputs a noise reduced signal 720 advantageously having a lower signal-to-noise ratio than any of the signals 702 from the sensors. The noise reduction module 700 may be the noise reduction module 307 described with respect to FIG. 3, or some other noise reduction module. Additionally, the noise reduction module 700 may be compatible with the embodiments described with respect to FIGS. 6A and/or 6B.

The noise reduction module 700 can include front end componentry 704 configured to condition the analog electrical signals 702 received from the acoustic sensors for processing. For example, the front end componentry 704 of one embodiment comprises a preamplifier, filter (e.g., high pass filter), amplifier, and/or analog to digital converter. In other embodiments, other circuitry may be provided in addition to or instead of these circuit components.

A cross-correlation module 706 receives the conditioned signals 708 and is configured to calculate a cross correlation of the signals 708. For example, the cross-correlation module 708 may generate a measure of the similarity of the signals 708 from sensors as a function of a time-lag applied to one of the signals. The cross-correlation calculation is sometimes referred to as a sliding dot product or inner product of the signals 708, for example.

The cross-correlation module 706 of certain embodiments shifts one or more of the signals 708 across one or more of the other signals in time and multiplies the shifted and un-shifted signals 708 together. Based on this shifting and multiplying operation, the cross-correlation module 706 can determine the value of time shift at which the multiplication of the signals is at a maximum value, relatively close to a maximum value, or at a relatively large value. This point may be referred sometimes to as the point of maximum energy or correlation between the signals 708.

As discussed, measurement signals 708 from the plurality of sensors can include both components indicative of bodily sounds and components indicative of noise, such as environmental noise. The bodily sound components of each of the signals 708 are generally out-of-phase with respect to each other. In contrast, the noise sound components of each of the signals 708 are generally in-phase with respect to each other.

Because the bodily sound signal components are relatively large in amplitude in relation to the environmental noise components, the point of maximum energy determined by the correlation module 706 corresponds to a shift amount at which the signals 708 have been synchronized, or shifted to be "in-phase" with one another in time.

Additionally, the shift amount corresponding to the point of maximum energy will shift the noise components of the signals 708, which were originally in phase with respect one another, to be out of phase.

The noise reduction module 700 can advantageously be configured to shift one of the sensor signals 708 from one of the sensors with respect to the signal 708 from the other sensor so as to place the bodily signal components of the two signals in phase, thereby also shifting the noise signal components out of phase. The shifted and un-shifted signals can be combined (e.g., summed together) to form a noise reduced signal.

For example, the cross-correlation module 706 outputs a plurality of shift signals 712 indicative of the shift amount corresponding to the point of maximum energy between the signals 708. In the illustrated embodiment, the signal 716 from one of the sensors is used as a reference and is therefore not shifted. Delay modules 710 are configured to delay one or more of the signals 708 according to the shift signals 712 to generate time-shifted signals 714 corresponding to time-shifted versions of one or more of the sensor signals 708. An output module 718 generates a noise-reduced signal 720. For example, the output module 718 may implement a summing function which adds together the time shifted signals 714 from the with the un-shifted signal 716.

In some configurations, the delay amount and shift signal 712 are calculated periodically or generally continuously so that potential changes in the phase relationships between the components of the signals 708 can be dynamically or adaptively accounted for. For example, in some cases, the phase relationship between bodily sound components of the signals 708 and the noise components of the signals 708 may change when a patient's respiratory rate increases dramatically, when new noise sources are introduced into the monitoring environment, or for other reasons. Periodically adjusting the delay amount and corresponding shift value 712 to account for such changes may improve monitoring accuracy. In one embodiment, the cross-correlation module 706 calculates the delay amount and corresponding shift signal 712 once at the beginning of a measurement cycle.

In various embodiments, other techniques or variations of the techniques described above may be used to find the point of maximum energy between the signals and corresponding appropriate delay amount. For example, the noise rejection module may employ a "shift and add" approach may be used instead of a "shift and multiply" approach generally employed by the cross-correlation module 706. In such an embodiment, the time-shifted signal may be added to the other signal as it is shifted instead of being multiplied with the other signal. Other techniques may include variations of cross-correlation or generally any techniques capable of finding points of similarity or maximum energy between two signals.

FIG. 7 illustrates an embodiment including three sensors and three associated sensor signals 702. In other embodiments, the sensor system includes two sensors or more than three sensors and the noise reduction module 700 is configured to receive and process a corresponding number of sensor signals. In such embodiments, for example, the delay module 710 can be configured to delay more than two of the signals 708 so as to place the bodily sound components of the signals 708 in phase, and the noise components of the signals 708 out of phase. In the general case where there are n signals and one signal is used as a reference signal, n-1 of the signals are delayed with respect to the reference signal.

The various components of the noise reduction module 700 may be implemented in hardware, software, or a combination thereof. In one embodiment, the front-end componentry is implemented in analog circuitry while the cross-correlation module 706 and the delay module 708 are implemented in software running on a processor of a physiological monitor.

Figure 8:
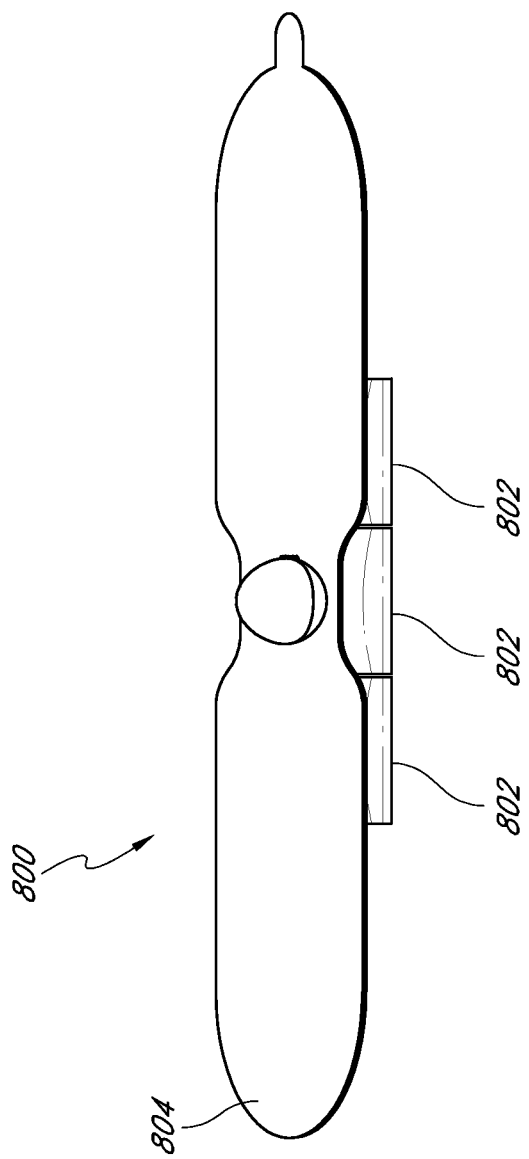
FIG. 8 is a perspective view of a multi-sensor arrangement including multiple sensor assemblies adjacent to one another according to embodiments of the disclosure.

FIG. 8 is a perspective view of a multi-sensor arrangement 800 including multiple sensor assemblies 802 adjacent to one another according to embodiments of the disclosure. The multi-sensor arrangement 800 may be configured to provide a noise reduced signal using signals from the individual sensor assemblies 802 according to embodiments described herein. The individual sensors 802 may be any of the sensors described herein such as the sensor 201 of FIG. 2, the sensors 312 of FIG. 3, the sensors 602 of FIGS. 6A-6B, or some other sensors.

In one embodiment, the signals from each sensor are communicated over separate conductors via the cable 804. In another embodiment, the signals from the multiple sensors 802 are communicated over the same conductor or conductors and the signals from the multiple sensors 802 are multiplexed or interleaved for communication between each of the sensors 802 and the monitor, or are otherwise sent over the single lead or wire. In other embodiments, the sensors 802 may not be chained together or otherwise connected, and separate cables connect the individual sensors 802 to the monitor.

In certain embodiments, the cable 804 may include one or more patient anchors such as those described herein for securing the cable to the patient and decoupling the attachment between the sensors 802 and the patient from movement of the cable due to movements such as accidental yanking or jerking. In one embodiment, one patient anchor is positioned in the region of the cable between the monitor and the first sensor 802 in the chain, and other patient anchors are positioned in the regions between each of the sensors 802 in the chain. Such arrangements can reduce accidental sensor disconnection.

Figure 9:
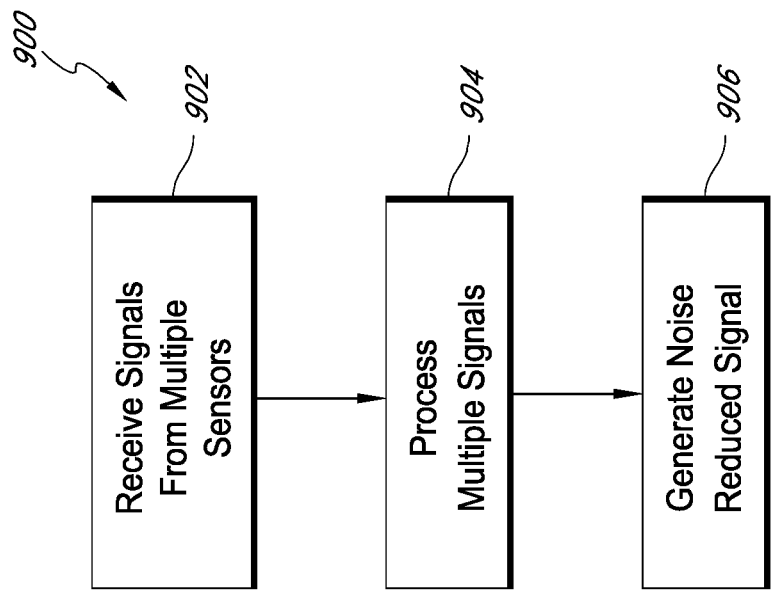
FIG. 9 is a flow chart illustrating a method of processing signals from a plurality of sensors in accordance with embodiments of the disclosure.

FIG. 9 is a flow chart illustrating a method 900 of processing signals from a plurality of sensors in accordance with embodiments of the disclosure. At step 902, the method 900 receives signals from multiple acoustic sensors attached to a patient at a plurality of measurement sites. Any number of acoustic sensors may be attached to the patient. For example, 2, 3, 4, 5 or more sensors may be applied in certain embodiments.

The multiple sensors may be arranged in and be compatible with any of the configurations described herein, such the configurations of FIGS. 6A and 6B. The method 900 may further be compatible with any of the noise reduction embodiments described herein. For example, the method 900 may be compatible with and perform the noise reduction function of the noise reduction modules 300, 500 of FIGS. 3 and/or 7.

As discussed herein with respect to FIGS. 6A-8, the received signals may include bodily sound components which are out of phase with respect to the bodily sound components of the signals from the other sensors and noise components which are in phase with respect to the noise components of the signals from the other sensors.

At step 904, the method 900 processes the multiple signals. For example, the method 900 may perform a cross-correlation operation so as to detect a time shift of the bodily signal components of the signals from the multiple sensors with respect to each other. In other embodiments, the method 900 may perform some other cross-correlation function, or some other technique to identify a time shift between bodily sound components of the signals.

At step 906, in one embodiment, the method 900 generates a noise reduced signal. For example, the method 900 may shift one or more of the sensor signals so as to generally line up the bodily sound components of the sensor signals with respect to the bodily sound components of the signals from the other sensors. The shift may also advantageously move the noise components of the sensor signals into an out of phase relationship with respect to the noise components from the other sensors.

At step 906, the method 900 further combines the shifted and un-shifted sensor signals so as to generate a noise reduced signal. For example, the bodily sound components of the signals from the multiple sensors may constructively combine or interfere, while the noise sound components do not, resulting in a signal having an improved signal to noise ratio.

Active Sensing

FIG. 10A schematically illustrates a sensor system 1000 including an acoustic sensor 1002 configured to both transmit acoustic vibrations 1004 into a measurement site 1006, and receive and sense acoustic vibrations 1008 from the measurement site. In such embodiments, the sensor 1002 can be used for other beneficial purposes in addition to measuring physiological parameters. For example, an acoustic signal 1004 can be transmitted into the skin of the patient 1005 at a measurement site 1006 and the acoustic response signal 1008 from the measurement site 1006 can be detected and processed so as to characterize a measurement site parameter. Such parameters can include tissue type at the measurement site 1006, the integrity of the mechanical connection between the sensor and measurement site 1006, etc.

Such information can advantageously be used for sensor calibration, alerting medical personnel (e.g., to probe-off conditions), and the like. A sensor 1002 having transmission and reception functionality may sometimes be referred to as an "active" sensor because it is capable of actively sending a signal into the measurement site 1006 to generates a response 1008, as well as passively receiving acoustic vibrations (e.g., from bodily sounds).

A sensing element 1012 of the sensor 1002 may be any of the sensing elements described herein, or some other sensing element 1012. In one embodiment, the sensing element 1012 may include a piezoelectric device such as a piezoelectric membrane. As described herein, piezoelectric membranes may be configured to convert mechanical deformations, such as those caused by acoustic vibrations coming from the patient's skin at a measurement site, into an electric voltage.

Additionally, in certain embodiments, a voltage may be applied to the piezoelectric membrane so as to actively deform the membrane. Modulation of the voltage applied to the membrane can thus cause it to vibrate, thereby emitting acoustic vibrations 1004 into the measurement site 1006. For piezoelectric sensing elements 1012, electrical signal values corresponding to received vibrations of a certain intensity can be much lower than the electrical signal values used to actively vibrate the sensor at a similar intensity. Thus, the sensing element 1012 may be characterized as lacking reciprocity with respect to transmission and reception of acoustic waves. To address the lack of reciprocity, a relatively high voltage driver may be used to drive the sensing element 1012 and generate the emitted vibrations 1004.

Although the arrows representing the emitted and detected acoustic vibrations 1004, 1008 are shown as leaving from different sides of the sensing element 1012, this is for the purposes of illustration only and is not limiting. Indeed, the emitted and detected acoustic vibrations 1004, 1008 may be transmitted and received from the same sensing element 1012 portion.

Acoustic vibrations 1008 may be generated from the measurement site 1006 (e.g., from the patient's skin) in response to the vibrations 1004 transmitted into the measurement site by the sensor 1002. The acoustic vibrations 1008 are received by the sensing element 1012 and may then be converted into an electrical signal which is then processed by the sensor system 1000. For example, a processor in the monitor 1014 may process the acoustic response 1008.

For example, the monitor 1014 may process a received signal including both (1) the acoustic response signal 1008 generated in response to the transmitted signal 1008 and (2) acoustic vibrations from bodily noises (e.g., respiratory rate, etc.) not associated with the acoustic response signal 1008. In certain embodiments, modulation of the driver signal is used to distinguish the signals. For example, in one embodiment, the transmitted signal includes bursts with a specific embedded pattern or signature. A lock filter is then used to identify only received signals including the pattern or signature will be identified as signals 1008 generated in response to the transmitted signal 1004. In other configurations, various forms of frequency or amplitude modulation may be employed.

In certain embodiments, instead of using modulation, a baseline reading is taken of the bodily noises (e.g., the patient's breathing) not associated with the response signal 1008. The baseline can then be subtracted from the received signal so that the sensor system can distinguish the normal bodily noises from the acoustic response signal 1008. In other embodiments, a filter (e.g., a high-pass, low-pass or band-pass filter) or some other mechanism may be used instead of, or in addition to the baseline approach to distinguish the acoustic response signal 1008.

Because various measurement sites will have certain characteristic acoustic responses 1008, the acoustic response 1008 can beneficially be used to determine a parameter (e.g., to characterize the measurement site 1006 and/or the connection between the measurement site 1006 and the sensor 1002). The information can then be intelligently used by the sensor system 1000. For example, the sensor system 1000 may use the information to calibrate the sensor, provide diagnosis, etc.

In one embodiment, the acoustic response 1008 is processed to identify whether or not the sensor 1002 is attached to a measurement site 1006. For example, the sensor system 1000 may determine whether or not the sensor 1002 is appropriately attached to human skin. If not, the system 1000 may provide an alarm or other probe-off indication. In certain embodiments, based on the acoustic response 1008, the sensor system 1000 may enable or disable sensor 1002 operation. The sensor system 1000 may disable the sensor 1002 in a probe-off situation, for instance. In other embodiments, the sensor system 1000 may determine a probe-off situation by detecting whether or not the sensor 1002 is attached to a solid object.

The system 1000 may determine the integrity of the connection between the sensor 1002 and the measurement site 1006 in certain embodiments. For example, given a known type of measurement site (e.g., skin), the total energy received in response to the acoustic vibrations 1004 may be indicative of the strength of the connection between the sensor 1002 and the measurement site 1006.

Such information may then be used to calibrate the sensor 1002, enable or disable the sensor 1002, or provide information to the user (e.g., communicate to the user that there is a weak sensor/measurement site connection). In an embodiment, if a relatively weak connection is detected, the system 1000 may increase the gain of the sensor 1002.

In other embodiments, the sensor system 1000 may provide detailed information regarding the measurement site. For example, the sensor system 100 may be able to characterize parameters such as tissue composition (e.g., fat and water percentage composition), tissue type, etc.

In processing the response signal 1008, the sensor system 1000 may, in certain embodiments, access a library of responses. For example, the system 1000 may compare the received response to entries in the library. In one embodiment, the response signal 1008 is compared to a series of previously recorded responses for various types of tissue (e.g., tissue of a particular region of the body, tissue having a particular composition, etc.).

In some embodiments, a library specific to the patient is generated and used for analyzing future response signals 1008. For example, in one embodiment acoustic responses 1008 are generated while the sensor 1002 is attached to various regions of a patient's body and the responses are stored in a library. Once the library is generated, future responses 1008 can be characterized by comparing the responses 1008 to those in the library.

Based on the comparison of the response signal 1008 with those recorded and stored in the library, various parameters such as the type of tissue, characteristic of the tissue, the integrity of the connection between the sensor and the measurement site, etc., may be determined. Such parameters may then be used by the system 1000 for beneficial purposes, such as for calibrating the sensor, providing diagnostic information, providing probe-off indications, etc.

The acoustic vibrations 1004 can be transmitted a depth d into the measurement site 1006 (e.g., a patient's skin). In certain embodiments, the acoustic vibrations 1004 may penetrate relatively deeply into the patient's skin, for example, allowing for improved parameter determination such as improved characterization of the measurement site. In other embodiments, the acoustic vibrations measure a response at the surface of the measurement site 1006. In some embodiments, the intensity or other parameter (e.g., frequency) of the transmitted acoustic signal 1004 can be controlled in order to adjust the level of penetration into the patient's skin 1005.

In certain embodiments, active sensing can be used for enhanced respiratory monitoring. For example, in one embodiment the sensor 1002 is configured to emit the transmitted signals 1004 to a depth sufficient to reach airway walls, the tissue walls that define the patient's respiratory airways. Airway walls are generally the surfaces that move from respiratory airflows, creating respiratory sounds. For example, the transmitted signal 1004 reaches the tracheal wall in one embodiment.

In such cases, the response signal 1008 is reflected off of the airway wall, received by the sensor 1002 and processed to sense the respiratory sounds of the patient. As described, the system filters out received signals other than the signals 1008 generated directly in response to the transmitted signal 1004 (e.g., using a signature and lock filter). Non-respiratory sound noise is removed. Additionally, distorting effects from the tissue that the reflected response signal 1008 travels through from the airway wall to the sensor is also removed.

As such, an active respiratory monitoring technique using the active sensor 1002 beneficially provides detection of respiratory sounds effectively at the source (the airway wall), providing highly accurate respiratory measurements. Moreover, respiratory sounds from precise locations in the patient's respiratory system may be targeted and detected using active respiratory sensing.

The active sensor functionality is periodically employed during sensor use in some embodiments. For example, in one embodiment, the transmitted acoustic signal 1004 is generated and the response 1008 is measured and processed at regular intervals. For example, the system 1000 may interrupt the normal sensor functionality of measuring acoustic vibrations indicative of various physiological parameters (e.g., respiratory rate, etc.) at regular intervals. During those intervals, the active sensor functionality described herein can be employed to determine a parameter (e.g., to detect probe-off, calibrate the sensor, etc.).

In one embodiment, the interval period is one second. Other intervals may include intervals from between 2 and 60 seconds, less than one second, or greater than 60 seconds. In some embodiments, the normal sensor functionality and the active sensor functionality are performed generally at the same time and the normal sensor functionality is not interrupted.

As shown in FIG. 10B, more than one sensing element 1012 may be used in certain embodiments. For example, the sensor 1002 may include first and second sensing elements 1012a, 1012b. In one embodiment, the first sensing element 1012a is actuated to transmit the acoustic signal 1004 into the measurement site 1006, and the response signal 1008 received by the second sensing element 1012b is processed by the system 1000. Other embodiments may include more than two sensing elements 1012, two or more separate sensors 1002, etc.

The processing of the acoustic response 1008 is described with respect to FIG. 10 as being implemented in the monitor 1014. In various other embodiments, the acoustic response 1008 may be processed, at least in part, in some other location in the sensor system 1000, such as on a processor of the sensor 1002, for example.

FIG. 11 is a flow chart illustrating a method 1100 of using an acoustic sensor in an active configuration. The acoustic sensor is generally capable of both transmitting acoustic signals into a measurement site of a patient and receiving acoustic signals from the measurement site so as to determine a parameter. For example, the acoustic sensor may be one of the acoustic sensors 1002 of FIGS. 10A-B, or may be some other acoustic sensor.

At step 1102, the method 1100 transmits a first acoustic signal into a measurement site with the sensor. For example, a voltage may be applied to a piezoelectric sensing element of the sensor so as to vibrate the sensing element and transmit acoustic sound waves into the measurement site.

At step 1104, the method 1100 receives a second acoustic signal from the measurement site. The second acoustic signal is generated in response to the transmitted signal. For example, certain tissues and other materials may generate characteristic acoustic signals in response to the first acoustic signal.

At step 1104, the method 1100 may also receive acoustic signals indicative of bodily or other noises not generated in response to the first acoustic signal. In such cases, the method 1100 may distinguish the second acoustic signal from the other sounds, such as by using a baseline, some type of filter, or a combination thereof, as described with respect to FIG. 10A-B above.

At step 1106, the method 1100 processes the second acoustic signal. For example, the method 1100 may be processed so as to determine one or more parameters, such as to characterize the tissue, determine the integrity of the mechanical connection between the sensor and measurement site, or for other purposes. Such information can advantageously be used for sensor calibration, alerting medical personnel (e.g., to probe-off conditions), and the like.

Additional Example Sensor System

Figure 12:
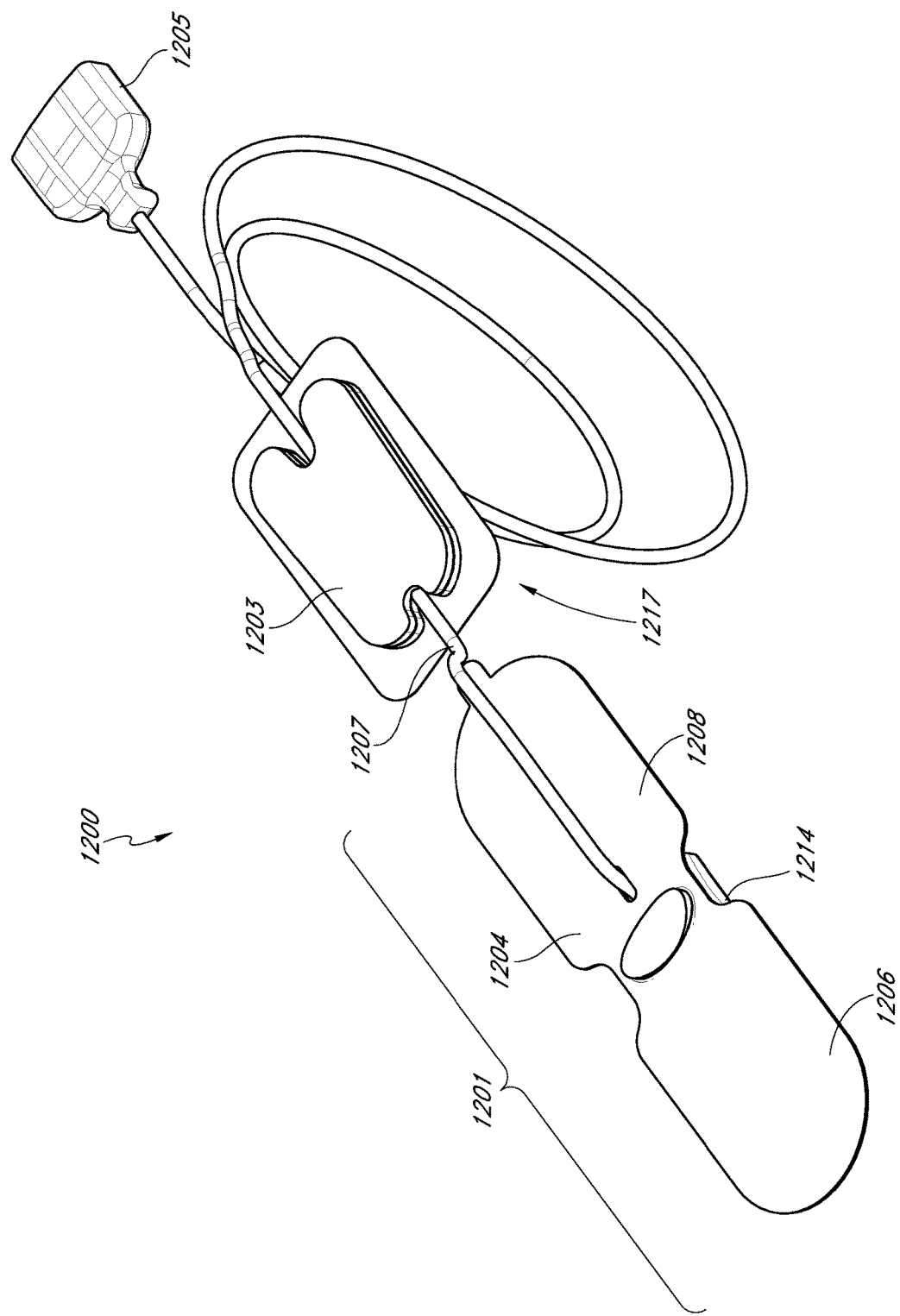
FIG. 12 is a top perspective view illustrating portions of another example sensor system in accordance with an embodiment of the disclosure.

FIG. 12 is a top perspective of a sensor system 1200 that includes a sensor 1201 suitable for use with any of the physiological monitors shown in FIGS. 1A-C and with various embodiments described herein. The sensor system 1200 also includes a cable 1207. The sensor 1201 includes an attachment element 1204 and an acoustic coupler 1214 enclosing various components of the sensor 1201. The cable 1207 of one embodiment includes a patient anchor 1203. The cable 1207 includes a connector 1205 removably attachable to a monitor connector (not shown) connectable to a physiological monitor (not shown) through another section of cable (not shown).

In various embodiments, not all of the components illustrated in FIG. 12 are included in the sensor system 1200. For example, in various embodiments, one or more of the patient anchor 1203 and the attachment element 1204 are not included. In one embodiment, for example, a bandage or tape is used instead of the attachment element 1204 to attach the sensor 1201 to a measurement site. Moreover, such bandages or tapes may be a variety of different shapes including generally elongate, circular and oval, for example.

The acoustic sensor 1201 of certain embodiments includes a sensing element (not shown), such as, for example, a piezoelectric device or other acoustic sensing device. The sensing element generates a voltage that is responsive to vibrations generated by the patient, and the sensor includes circuitry to transmit the voltage generated by the sensing element to a processor for processing. In an embodiment, the acoustic sensor 1201 includes circuitry for detecting and transmitting information related to biological sounds to a physiological monitor. These biological sounds may include heart, breathing, and/or digestive system sounds, in addition to many other physiological phenomena. The acoustic sensor 1201 in certain embodiments is a biological sound sensor, such as the sensors described herein. In some embodiments, the biological sound sensor is one of the sensors such as those described in the '883 Application, the '939 Application. In other embodiments, the acoustic sensor 1201 is a biological sound sensor such as those described in U.S. Pat. No. 6,661,161, which is incorporated by reference herein. Other embodiments include other suitable acoustic sensors. For example, in one embodiment, the sensor 1201 is configured to be attached to a patient and includes a sensing element configured to detect bodily sounds from a patient measurement site.

The sensing element may include a piezoelectric membrane, for example, and is supported by a support structure such as a generally rectangular support frame. The piezoelectric membrane is configured to vibrate in response to acoustic vibrations, which generates electrical signals indicative of the bodily sounds of the patient at the membranes poles. Example sensing elements compatible with embodiments disclosed herein are disclosed in the '939 Application. For example, sensing elements are described and/or shown in and described with respect to FIGS. 2A-3C and 6A-6E of the '939 Application.

The acoustic sensor 1201 may also include an electrical shielding barrier, providing for beneficial electrical shielding of a sensing element, such as a piezoelectric element of the sensor, from external electrical noises. The electrical shielding barrier can include one or more layers which form a Faraday cage around the piezoelectric element, for example, and which distribute external electrical noise substantially equally to first and second electrical poles of the piezoelectric sensing element. In addition, the shielding barrier flexibly conforms to the surface shape of the piezoelectric element as the surface shape of the piezoelectric element changes, thereby improving the shielding and sensor performance. Examples of shielding barriers compatible with embodiments disclosed herein are shown in and described with respect to FIGS. 2B-2E and 6B-6E of the '939 Application.

The sensor 1201 of the illustrated embodiment includes an acoustic coupler 1214 which in one embodiment envelops or at least partially covers some or all of other components of the sensor 1201. The bottom of the acoustic coupler 1214 includes a contact portion 1216 which is brought into contact with the skin of the patient. The acoustic coupler 1214 is configured to transmit bodily sound waves to the sensing element and improves the coupling between the source of the signal to be measured by the sensor (e.g., the patient's skin) and the sensing element. Improved coupling provides an increased signal to noise ratio. The acoustic coupler 1214 of one embodiment includes a bump positioned to apply pressure to the sensing element so as to bias the sensing element in tension. Example acoustic couplers compatible with embodiments described herein shown in and described with respect to FIGS. 2A-2E, 4, 5A-5B and 6A-6E of the '939 Application.

The attachment element 1204 includes first and second elongate portions 1206, 1208. The first and second elongate portions 1206, 1208 can include patient adhesive (e.g., in some embodiments, tape, glue, a suction device, etc.) attached to a resilient backbone (not shown). The adhesive on the elongate portions 1206, 1208 can be used to secure the sensor 1201 to a patient's skin. The attachment element 1204 can beneficially bias the sensor 1201 in tension against the patient's skin and reduce stress on the connection between the patient adhesive and the skin. A removable backing can be provided with the patient adhesive to protect the adhesive surface prior to affixing to a patient's skin. Examples of attachment elements compatible with embodiments described herein are shown in and described with respect to FIGS. 2A, 9A-9D, and 10 of the '939 Application.

The sensor cable 1207 is electrically coupled to the sensor 1201 via a printed circuit board ("PCB") (not shown) residing in the sensor 1201. Through this contact, electrical signals are communicated from the multi-parameter sensor 1201 to the physiological monitor through the may advantageously secures the sensor to the patient at a point between the ends of the sensor cable 1207. The patient anchor 1203 attached to the cable 1207 advantageously secures the sensor to the patient at a point between the ends of the cable 1207. Securing the cable 1207 to the patient can decouple movement of the cable 1207 due to various movements such as accidental yanking or jerking on the cable 1207 or movement of the patient. Such decoupling advantageously reduces the noise detected by the sensor when the cable 1207 is moved. Patient anchors compatible with embodiments described herein are shown in and described with respect to FIGS. 2A, 11A-B and 12 of the patent application entitled, "ACOUSTIC SENSOR ASSEMBLY", for example.

Terminology/Additional Embodiments

The modules described herein of certain embodiments may be implemented as software modules, hardware modules, or a combination thereof. In general, the word "module," as used herein, can refer to logic embodied in hardware or firmware or to a collection of software instructions executable on a processor. Additionally, the modules or components thereof may be implemented in analog circuitry in some embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. An acoustic sensor configured to non-invasively detect physiological acoustic vibrations indicative of one or more physiological parameters of a medical patient, comprising:
    a piezoelectric membrane configured to generate an initial signal in response to acoustic vibrations from a medical patient, the initial signal having an amplitude;
    front-end circuitry configured to receive an input signal that is based at least in part on the initial signal and to produce an amplified signal in response to the input signal; and
    a compression module in communication with the front-end circuitry and configured to:
        select a first compression scheme of a plurality of dynamic range compression schemes, wherein different dynamic range compression schemes of the plurality of dynamic range compression schemes correspond to different modifications to signals;
        compress a first portion of the initial signal according to the first compression scheme to generate a first compressed portion, the first portion of the initial signal having a magnitude of the amplitude that is greater than a predetermined threshold level,
        wherein a second portion of the initial signal remains uncompressed by the compression module, the second portion corresponding to a portion of the initial signal having a magnitude of the amplitude that is less than the predetermined threshold level,
        wherein the first compressed portion corresponds to a physiological sound louder than breathing, and
        wherein the second portion corresponds to a breathing sound;
        detect a characteristic of the initial signal;
        select a second compression scheme of the plurality of dynamic range compression schemes based at least on the characteristic of the initial signal, wherein the second compression scheme is different from the first compression scheme; and
        compress a third portion of the initial signal according to the second compression scheme to generate a compressed third portion; and
        provide the input signal to the front-end circuitry, wherein the input signal comprises at least the first compressed portion, the second portion, and the third compressed portion.

2. The acoustic sensor of claim 1, wherein the third portion of the initial signal has a magnitude of the amplitude that is greater than a second predetermined threshold level different from the predetermined threshold level, wherein the magnitude of the amplitude of the first portion of the initial signal is less than the second predetermined threshold level.

3. The acoustic sensor of claim 1, wherein the first compression scheme is selected to increase a dynamic range of the acoustic sensor.

4. The acoustic sensor of claim 1, wherein the first compression scheme is selected based on a dynamic range of the front-end circuitry.

5. The acoustic sensor of claim 1, wherein the first compression scheme is selected such that the acoustic sensor does not produce a distorted output when high-amplitude physiological sounds are detected by the piezoelectric membrane, the high-amplitude physiological sounds corresponding to a portion of the initial signal having a magnitude of the amplitude corresponding to a saturation level of the front-end circuitry.

6. The acoustic sensor of claim 1, wherein the front-end circuitry comprises a preamplifier.

7. The acoustic sensor of claim 1, wherein the first compression scheme comprises executing a logarithmic function.

8. The acoustic sensor of claim 1, wherein the first compression scheme comprises executing a linear function.

9. The acoustic sensor of claim 8, wherein the linear function comprises a piece-wise linear function.

10. The acoustic sensor of claim 1, wherein the first compression scheme comprises executing a non-linear function.

11. An acoustic sensor configured to non-invasively detect physiological acoustic vibrations indicative of one or more physiological parameters of a medical patient, comprising:
    an acoustic sensing element configured to generate an initial signal in response to acoustic vibrations from a medical patient, the acoustic sensing element having an output dynamic range, and the initial signal having an amplitude;
    front-end circuitry in communication with the acoustic sensing element and having a dynamic range, the dynamic range of the front-end circuitry being less than the output dynamic range of the acoustic sensing element, wherein the front end circuitry is configured to produce an amplified signal based at least partly on the initial signal; and
    a dynamic range module configured to:
        select a first compression scheme of a plurality of dynamic range compression schemes, wherein different dynamic range compression schemes of the plurality of dynamic range compression schemes correspond to different modifications to signals;
        modify at least a first portion of the amplified signal to generate a modified first portion by compressing at least the first portion of the amplified signal according to the first compression scheme, the first portion of the amplified signal corresponding to a portion of the initial signal having a magnitude of the amplitude that is greater than a predetermined threshold level, wherein the modified first portion of the amplified signal corresponds to a physiological sound louder than breathing, wherein a second portion of the amplified signal remains unmodified by the dynamic range module, the second portion of the amplified signal corresponding to a portion of the initial signal having a magnitude of the amplitude that is less than the predetermined threshold level, wherein the second portion of the amplified signal corresponds to a breathing sound;
        detect a characteristic of the amplified signal;
        determine, based at least on the characteristic, to change from using the first compression scheme to using a second compression scheme of the plurality of dynamic range compression schemes; and
        modify a third portion of the amplified signal according to the second compression scheme to generate a modified third portion, wherein output from the dynamic range module comprises at least the modified first portion, the second portion, and the modified third portion.

12. The acoustic sensor of claim 11, wherein the dynamic range of the front-end circuitry is an input dynamic range.

13. The acoustic sensor of claim 11, wherein the dynamic range module is configured to modify the first portion of the amplified signal to allow the sensor to process a desired range of physiological intensities without producing a distorted output.

14. The acoustic sensor of claim 11, wherein the dynamic range module performs logarithmic compression on at least the first portion of the amplified signal.

15. The acoustic sensor of claim 11, wherein the dynamic range module performs linear compression on at least the first portion of the amplified signal.

16. The acoustic sensor of claim 15, wherein the linear compression comprises piece-wise linear compression.

17. The acoustic sensor of claim 11, wherein the dynamic range module performs non-linear compression on at least the first portion of the amplified signal.

18. A method comprising:
    outputting an initial AC signal using a first sensing element and in response to acoustic vibrations from a medical patient, the initial AC signal having an amplitude;
    generating an amplified signal using front-end circuitry and in response to an input signal that is based at least in part on the initial AC signal;
    selecting a first compression scheme of a plurality of dynamic range compression schemes, wherein different dynamic range compression schemes of the plurality of dynamic range compression schemes correspond to different modifications to signals;
    compressing portions of the amplified signal according to the first compression scheme, wherein the initial AC signal varies in amplitude about a DC offset and the compressed portions correspond to portions of the initial AC Signal deviating in amplitude from the DC offset by greater than a predetermined threshold level, and at least a portion of the amplified signal corresponding to a breathing sound remains uncompressed and at least a portion of the amplified signal corresponding to a physiological sound louder than breathing is compressed;
    detecting a characteristic of the amplified signal;
    determining, based at least on the characteristic, to change from using the first compression scheme to using a second compression scheme of the plurality of dynamic range compression schemes; and
    compressing additional portions of the amplified signal according to the second compression scheme.

19. The method of claim 18, wherein the initial AC signal comprises positive and negative peaks and wherein the compressed portions correspond to both positive and negative peaks of the initial AC signal which deviate from the DC offset by greater than the predetermined threshold.

20. The method of claim 18, wherein the compressed portions correspond to only positive peaks of the initial AC signal which deviate from the DC offset by greater than the predetermined threshold.

21. The acoustic sensor of claim 1, wherein the characteristic of the initial signal comprises at least one of: a type of sound represented by the initial signal; an intensity, for a time period, of a sound represented by the initial signal; or a saturation of a component of the acoustic sensor by the initial signal.

22. The acoustic sensor of claim 11, wherein the acoustic sensing element is further configured to:
 transmit first acoustic vibrations to a measurement site of the medical patient;
 sense second acoustic vibrations from the measurement site; and
 determine, based at least partly on the second acoustic vibrations, a characteristic of a mechanical connection between the acoustic sensing element and the measurement site.

23. The method of claim 18, further comprising:
 comparing a signal deviation of a second portion of at least one of the initial AC signal or the amplified signal to a first sound signature of a plurality of sound signatures, the first sound signature associated with a respiratory condition;
 determining, based at least partly on comparing the signal deviation of the second portion to the first sound signature, that the second portion corresponds to the first sound signature; and
 automatically initiating a communication regarding the respiratory condition.

24. The acoustic sensor of claim 1, further comprising a decompression module configured to modify the amplified signal to reduce an effect of the compression module on the amplified signal.

* * * * *